US012150888B2

(12) United States Patent
Augustine et al.

(10) Patent No.: US 12,150,888 B2
(45) Date of Patent: *Nov. 26, 2024

(54) ELECTRIC HEATING PADS AND MATTRESSES

(71) Applicant: Augustine Temperature Management LLC, Eden Prairie, MN (US)

(72) Inventors: Scott D. Augustine, Deephaven, MN (US); Ryan S. Augustine, Minneapolis, MN (US); Garrett J. Augustine, Long Lake, MN (US); Brent M. Augustine, Savage, MN (US); Randall C. Arnold, Minnetonka, MN (US); John R. Beckman, New Brighton, MN (US)

(73) Assignee: Augustine Temperature Management LLC, Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/581,243

(22) Filed: Feb. 19, 2024

(65) Prior Publication Data
US 2024/0189141 A1    Jun. 13, 2024

Related U.S. Application Data

(63) Continuation of application No. 18/066,048, filed on Dec. 14, 2022, now Pat. No. 11,903,870, which is a (Continued)

(51) Int. Cl.
*A61F 7/00* (2006.01)
*A47C 21/04* (2006.01)
*H05B 3/34* (2006.01)

(52) U.S. Cl.
CPC ............ *A61F 7/007* (2013.01); *A47C 21/048* (2013.01); *H05B 3/342* (2013.01);
(Continued)

(58) Field of Classification Search
CPC .......... A47C 21/048; A61F 2007/0071; A61F 2007/0077; A61F 2007/0086;
(Continued)

(56) References Cited

U.S. PATENT DOCUMENTS 10,201,935 B2    2/2019 Augustine et al.
10,206,248 B2    2/2019 Augustine et al.
(Continued)

OTHER PUBLICATIONS

International Search Report and Written Opinion for International Patent Application No. PCT/US2023/061183, mailed May 23, 2023, 12 Pages.

*Primary Examiner* — Dana Ross
*Assistant Examiner* — James F Sims, III
(74) *Attorney, Agent, or Firm* — Fredrikson & Byron, P.A.

(57) ABSTRACT

An electric heating pad for warming a patient includes a heated underbody support or heated mattress. The heated underbody support or mattress includes a heater assembly having a flexible sheet-like heating element, conductive bus bars attached at or near side edges of the heating element, and fabric side edge extensions attached to heating element side edges. The heated underbody support or mattress also includes a layer of polymeric foam positioned under the heater assembly and a shell, including at least two sheets of flexible material, covering at least a portion of the heater assembly and the layer of polymeric foam. When the heater assembly is wrapped around the top surface of the layer of polymeric foam, side edges of the heating element extend partially down the two side walls of the layer of polymeric foam and the conductive bus bars lie adjacent those two side walls.

21 Claims, 20 Drawing Sheets

Related U.S. Application Data continuation of application No. 17/583,747, filed on Jan. 25, 2022, now Pat. No. 11,534,334.

(52) U.S. Cl.
CPC .......... *A61F 2007/0071* (2013.01); *A61F 2007/0077* (2013.01); *H05B 2203/016* (2013.01)

(58) Field of Classification Search
CPC ............ A61F 2007/0096; A61F 7/007; H05B 2203/013; H05B 2203/014; H05B 2203/016; H05B 2203/017; H05B 3/145; H05B 3/342
USPC ................................................ 219/201, 387
See application file for complete search history.

(56) References Cited

U.S. PATENT DOCUMENTS

| | | |
|---|---|---|
| 10,506,668 B2 | 12/2019 | Augustine et al. |
| 10,575,784 B2 * | 3/2020 | Augustine ............ A61G 7/005 |
| 10,765,580 B1 | 9/2020 | Augustine |
| 10,849,193 B2 | 11/2020 | Augustine et al. |
| 2007/0067910 A1 | 3/2007 | Augustine et al. |
| 2009/0099631 A1 | 4/2009 | Augustine et al. |
| 2012/0279953 A1 | 11/2012 | Augustine et al. |
| 2015/0289817 A1 | 10/2015 | Augustine et al. |
| 2015/0290027 A1 | 10/2015 | Augustine et al. |
| 2015/0366367 A1 | 12/2015 | Augustine et al. |
| 2019/0217548 A1 | 7/2019 | Augustine et al. |
| 2020/0196955 A1 | 6/2020 | Augustine et al. |

\* cited by examiner

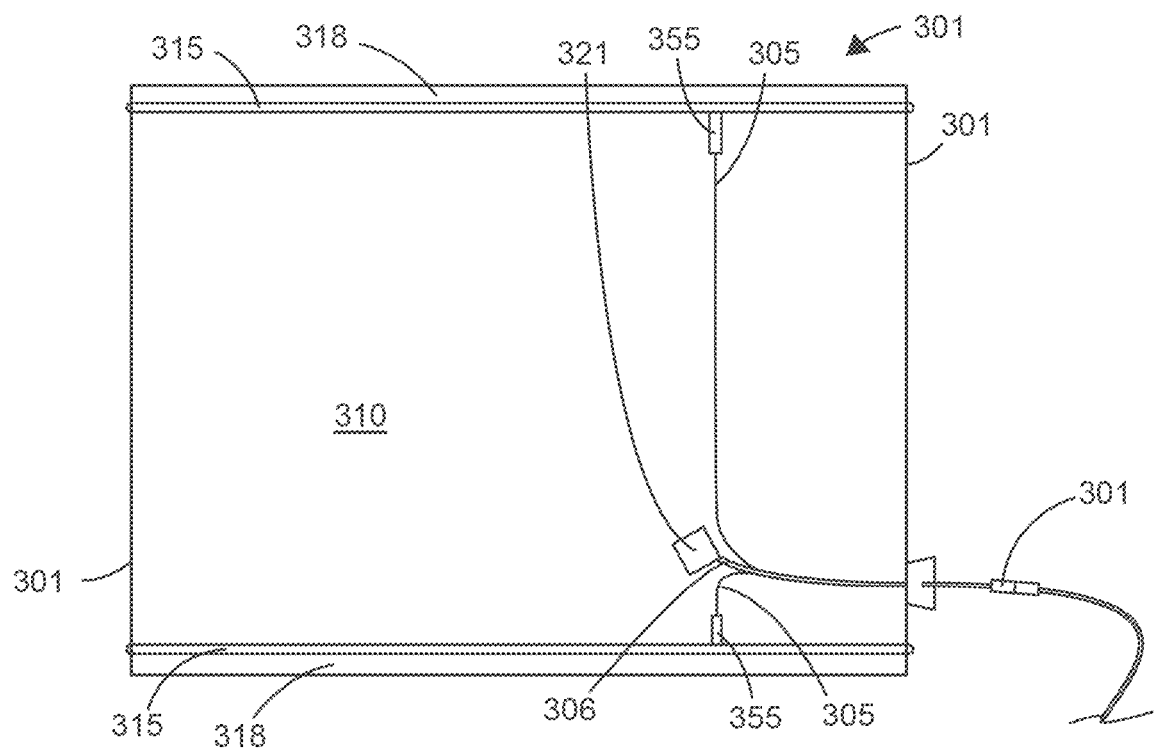
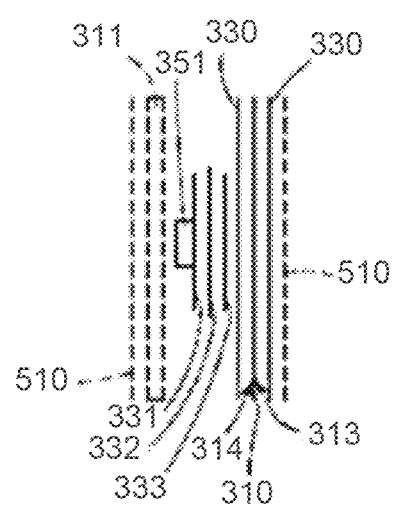
Fig. 3A
Fig. 3B

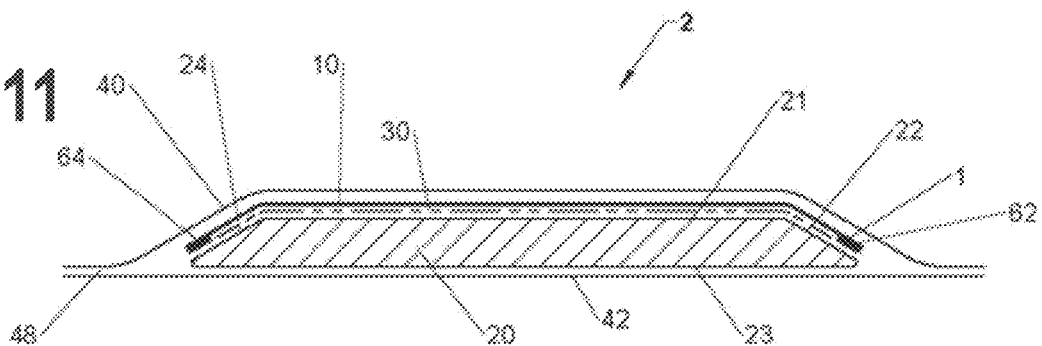
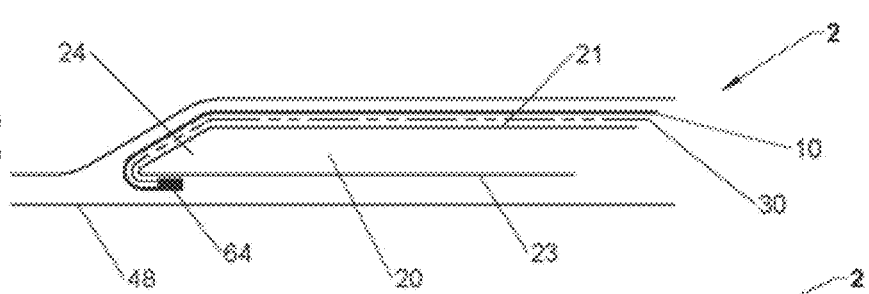
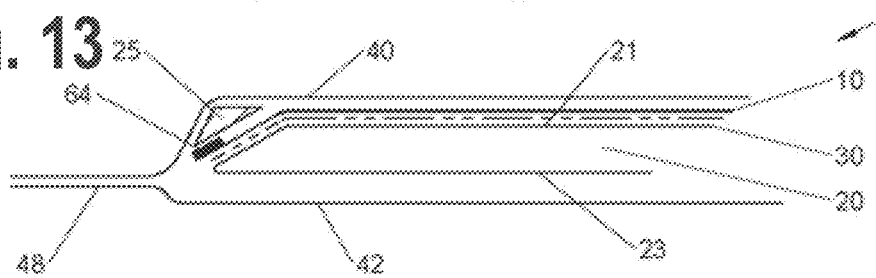
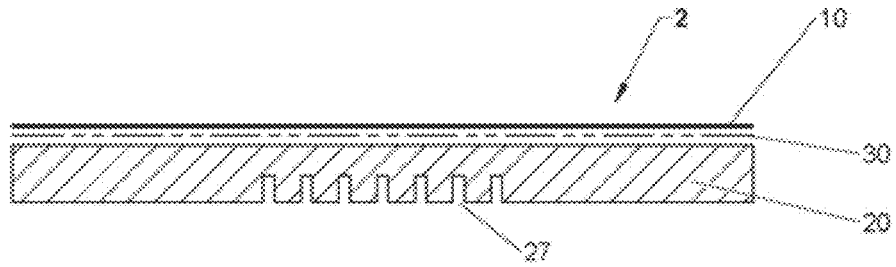

ELECTRIC HEATING PADS AND MATTRESSES

CROSS REFERENCE TO RELATED APPLICATION

This application is a continuation of U.S. patent application Ser. No. 18/066,048, filed Dec. 14, 2022, and titled "ELECTRIC HEATING PADS AND MATTRESSES", which is a continuation of U.S. patent application Ser. No. 17/583,747, filed Jan. 25, 2022, now U.S. Pat. No. 11,534,334, issued Dec. 27, 2022, and titled "ELECTRIC HEATING PADS AND MATTRESSES", the contents of which are incorporated herein by reference in their entirety.

TECHNICAL FIELD

The present disclosure relates to heater assemblies including heating or warming blankets, pads or mattresses, and more particularly to those including electrical heating elements.

BACKGROUND

It is well established that surgical patients under anesthesia become poikilothermic. This means that the patients lose their ability to control their body temperature and will take on or lose heat depending on the temperature of the environment. Since modern operating rooms are all air conditioned to a relatively low temperature for surgeon comfort, the majority of patients undergoing general anesthesia will lose heat and become clinically hypothermic if not warmed.

There have been many attempts at making heated blankets and pads, including pads in the form of heated underbody supports, heated mattresses and heated mattress overlays for therapeutic patient warming. Therapeutic patient warming is especially important for patients during surgery. It is well known that without therapeutic intra-operative warming, most anesthetized surgical patients will become clinically hypothermic during surgery. Hypothermia has been linked to increased wound infections, increased blood loss, increased cardiac morbidity, prolonged ICU time, prolonged hospital stays, increased cost of surgery and increased death rates.

Over the past 20 years, forced-air warming (FAW) has become one of the "standard of care" for preventing and treating the hypothermia caused by anesthesia and surgery. FAW consists of a large heater/blower attached by a hose to an inflatable air blanket. The warm air is distributed over the patient within the chambers of the blanket and then is exhausted onto the patient through holes in the bottom surface of the blanket.

Although FAW is clinically effective, it suffers from several problems including: a relatively high price; air blowing in the operating room, which can be noisy and can potentially contaminate the surgical field; and bulkiness, which, at times, may obscure the view of the surgeon. Moreover, the low specific heat of air and the rapid loss of heat from air require that the temperature of the air, as it leaves the hose, be dangerously high—in some products as high as 45° C. This poses significant dangers for the patient. Second and third degree burns have occurred both because of contact between the hose and the patient's skin, and by blowing hot air directly from the hose onto the skin without connecting a blanket to the hose. This condition is common enough to have its own name—"hosing." The manufacturers of forced air warming equipment actively warn their users against hosing and the risks it poses to the patient.

To overcome the aforementioned problems with FAW, several companies have developed electric warming blankets. Some of these warming blankets employ flexible heaters, the flexibility of which is desirable to maintain when employing the blankets. In many cases, an electric warming blanket employs a shell for holding the heater and for serving other purposes. For example, in some cases the shell includes layers formed of a substantially water impermeable material to help prevent fluid damage to the heater. Also, when these heaters are used for patient or other care, especially in the operating room, the shell can protect the patient and others in the vicinity from electric shock hazards. In addition to often providing a seal around the heater, the shell often contains a fastening mechanism that must reliably attach the heater to the shell to prevent electrical shorting across the heater during folding of the electric warming blanket.

Because the seals of the shell must be very reliable, the seals have traditionally been adhesive seals that are reinforced with combinations of sewing, rivets, and grommets. Sewing stitches, rivets, and grommets all share one characteristic—they all perforate the material layers to create a mechanical linkage between the layers.

While such a reinforced bond may be desirable for strength, it can create additional problems when used during surgery or medical procedures. For example, heated blankets placed over a patient during a surgery or medical procedure are frequently soiled with waste blood or other body fluids. The fluid waste can saturate the stitching and then dry and accumulate in the thread or the stitch holes. If rivets or grommets are used for reinforcement, additional crevasses are introduced that can trap waste fluids. When the outer shell of the blanket is cleaned by hospital personnel, it is nearly impossible to clean the residual contaminating materials out of the holes, crevasses, and/or stitches. Therefore, the stitching holes and thread, the grommets, rivets and snaps can all become sources of microbial contamination because they cannot be thoroughly cleaned and disinfected.

Prior to the 1990's, warm water mattresses were commonly used. The warm water mattresses went out of common use because they were relatively stiff and inflexible. The stiff water mattress negated any pressure relief that the underlaying support mattress may have provided. As a result, the combination of pressure applied to the boney prominences and the heat from the warm water mattress both reduced blood flow and accelerated metabolism, causing accelerated ischemic pressure injuries to the skin ("bed sores"). Additionally, the warmed water recirculating in the warming system was well known to be grossly contaminated with bacteria, which was especially important when a leak occurred. As a result, warm water mattresses are rarely used today.

Historically, electrically heated pads and blankets for the consumer market have been made with resistive wire heaters. Wire-based heaters have been questionably safe in consumer use. However, in the operating room environment with anesthetized patients, hot spots caused by the wires in normal use and the failure mode of broken heater wires resulting in sparking, arcing and fires are totally unacceptable. Therefore, resistive wire-based heaters are not used in the operating room today.

Since the mid 1990's, a number of inventors have tried unsuccessfully to make effective and safe heated mattresses for operating room use, using flexible, sheet-like electric resistance heaters. The sheet-like heaters have been shown to be more effective in warming the patients because of the even heat production and generally do not cause arcing and sparking when they fail.

Some existing devices employ sheet-like heaters using a polymeric fabric that has been baked at high temperature until it becomes carbonized and is thus conductive of electricity. The carbonization process makes the fabric fragile, and therefore, it may be laminated between two layers of plastic film or fiber-reinforced plastic film for stability and strength. The lamination process results in a relatively stiff, although somewhat flexible, non-stretching, non-conforming heater. The metal foil bus bars are attached to the heater material with an "electrically conductive adhesive or bonding composition . . . " and then encapsulated with polyurethane-coated nylon fabric. The result is a stiff and relatively inflexible bus bar.

Clearly, there is a need for conductive fabric heaters for use in therapeutic heated mattresses that are highly flexible, stretchable in at least one direction and durable without needing lamination to stabilize or protect the heater fabric. There is also a need for bus bar construction that does not result in thick, stiff, inflexible areas along the side edges of the heater. Then, maximally effective and safe therapeutic heated mattresses need to be designed using the stretchable, durable fabric heaters.

Accordingly, there remains a need for heated blankets, shells and pads for flexible heaters that are readily and thoroughly cleanable. In particular, there is a need for devices including these features that also offer pressure relief and prevent bed sores.

Various embodiments of the invention described herein solve one or more of the problems discussed above in addition to other problems that will become apparent.

SUMMARY

Certain embodiments of the invention include a heater assembly such as an electric heating blanket, pad or mattress including a flexible sheet-like heating element and a shell. The shell covers the heating blanket, pad or mattress and includes two sheets of flexible material welded together. In some embodiments the weld couples the sheets together about the edges of the heating element. In some embodiments, the weld couples the sheets about the edges of the sheets. Although the heating blanket or pad is described as having two sheets welded together, as one of ordinary skill in the art would consider, the two sheets could be formed from one sheet folded over on itself to form the two different sheet layers.

Certain embodiments of the invention include a heater assembly such as an electric heating mattress including a flexible sheet-like heating element, a compressible material layer comprising a foam or air mattress pad, and a shell. The shell covers the heating mattress and includes two or more sheets of flexible material welded or sewn together. In some embodiments the heating element may be attached to the foam or air mattress pad and the heating element/mattress pad assembly is encased in the shell.

In some embodiments, the temperature sensor of the heated blanket, pad or mattress (e.g., underbody warming system, or heated underbody support) is located on the heater assembly, so that it senses the temperature of the heater assembly in contact with the patient. The temperature sensor thus also serves as a safety sensor, decreasing power to the heater assembly excess heat buildup under the patient from the electrosurgical grounding. The heater controller will alarm if the heater temperature exceeds a safe temperature for heating the skin whether the heating is due to the effect of the heater assembly or the capacitive grounding.

In some embodiments, the conductive or semi-conductive material is polypyrrole. In some embodiments the compressible material includes a foam material and in some embodiments it includes one or more air filled chambers. For example, in some embodiments of the heater assembly may be a blanket, pad or mattress that includes a water resistant shell encasing the heater assembly, including an upper shell and a lower shell that are sealed together along their edges to form a bonded edge. In some examples, the heater assembly is attached to the compressible material layer along one or more edges of the heater assembly. In some embodiments, the heated pad or mattress (e.g., heated underbody support pad) also includes a water resistant shell encasing the heater assembly, including an upper shell and a lower shell that are sewn together along their edges to form a sewn and bonded edge. In some embodiments, the heating element has a generally planar shape when not under pressure, is adapted to stretch into a 3 dimensional compound curve without wrinkling or folding while maintaining electrical conductivity in response to pressure, and to return to the same generally planar shape when pressure is removed.

Maximal patient warming effectiveness is achieved by maximally accommodating the patient into the mattress. In other words, maximizing the contact area between the patient's skin and the heated surface of the mattress. The heater and foam (compressible material) or air bladders of the mattress may be easily deformable to allow the patient to sink into the mattress. This accommodation maximizes the patients skin surface area in contact with the mattress and heater, which minimizes the pressure applied to any given point. It also maximizes the surface contact area for heat transfer and maximizes blood flow to the skin in contact with the heat for optimal heat transfer. The accommodation of the patient into the mattress may not be hindered by a stiff, non-conforming, non-stretching, hammocking heater. Additionally, the heater should be near the top surface of the mattress, in thermally conductive contact with the patient's skin, not buried beneath thick layers of foam or fibrous insulation.

In some embodiments, the compressible material comprises one or more flexible air filled chambers. In some embodiments, the compressible material is a foam material. The heater assembly may be attached to the top surface of the layer of compressible material. In some examples, the heater assembly may not be attached to the top surface of the layer of compressible material but instead wrapped around the sides of the compressible material and attached to the back side of the compressible material. In some examples, having the heater assembly unattached to the top surface of the layer of compressible material, and instead attached around the sides, can prevent the stiffness and non-conformability created by the adhesive lamination of material layers and can help to minimize hammocking by allowing lateral movement between the heater assembly and the compressible material layer. In some embodiments, the heated underbody support includes a water resistant shell encasing the heating assembly and compressible material and having an upper shell and a lower shell that are sealed together along their edges to form bonded edges. In some embodiments, one or more edges of the heater assembly may be sealed into the bonded edge. In some embodiments, the heater assembly is attached to the upper layer of water resistant shell material. In some embodiments, the heater assembly is attached to the shell only along one or more edges of the heater assembly. In some embodiments, the heated underbody support also includes an electrical inlet, wherein the inlet is bonded to the upper shell and the lower shell and passes between them at the bonded edge.

Electrically heated mattresses are compressible and accommodating, thus the patients sink into the mattress and more body surface area is recruited to help support the weight of the patient. If the proper foam materials are chosen, virtually the entire posterior surface of the patient contacts the mattress. However, even with the added contact surface area, these mattresses are incapable of transferring enough heat to maintain patient normothermia, especially in pediatric patients.

In some examples, the heating element may extend across the width (e.g., the entire width) of the upper surface of the foam or air compressible material layer and extend at least part way down the side wall of the foam or air compressible material layer. The electrical buss bars attached along the side edges of the heater can thus advantageously located against a side wall of the compressible material layer. In this position, the buss bars can be protected from flexing at each instance a patient sits on, or otherwise applies a load on, the mattress. In some examples, the heating element and buss bars are unattached to the side walls of the foam compressible material layer to allow free movement within the interior of the foam compressible material and prevent sharp flexing. In some examples, the heater assembly is not adhesively attached across the whole top surface of the foam compressible material layer, to allow movement against the foam which reduces "hammocking."

In some examples, the heater assemblies include nonconductive fabric attachment extensions sewn to the edges of the heating element. In some such examples, these nonconductive fabric attachment extensions can wrap around the sides of the compressible material layer and adhesively attach to the bottom surface (under side, opposite the top surface) of the compressible material layer.

In some examples, the heater assemblies may be covered on their top and/or bottom surfaces with a layer of oxygen barrier polymeric film in order to protect the heating element from oxidizers, such as, for instance, peroxide and oxygen. In some examples, the oxygen barrier polymeric film may be adhesively bonded to the heating element.

In some examples, a pressure actuator (e.g., a pressure sensor, such as a pressure switch) may be included near the control temperature sensor in order to detect the presence or absence of a patient laying on the mattress. In some examples, the temperature of the heater can be automatically reduced, or in some cases the heater can be turned off, if the pressure sensor has not detected the presence of a patient on the mattress for a preset period time (e.g., 5 minutes, 10 minutes, 15 minutes, etc.). This can prevent a heated mattress from over-heating in an area under a thermal insulator such as a pile of blankets for example.

In some examples, a non-conductive fabric end extension attached to the lower edge of the flexible sheet-like heating element can be adhesively attached to one or more to the top surface, the lower side and the lower surface of the layer of foam compressible material layer. The non-conductive fabric lower edge extension can be attached at the perineal cutout and adjacent the perineal cutout to reinforce the perineal cutout against pressures applied to it during Trendelenburg securement.

The following provides a numbered listing of exemplary embodiments that are within the scope of the present disclosure:

1. An electric heating pad for warming a patient, the electric heating pad comprising a heated underbody support or heated mattress, the heated underbody support or heated mattress comprising: a heater assembly comprising: a flexible sheet-like heating element including a top surface, a bottom surface, an upper edge, a lower edge, and at least two side edges, conductive bus bars including a first conductive bus bar attached at or near one of the at least two side edges of the heating element and a second conductive bus bar attached at or near another of the at least two side edges of the flexible sheet-like heating element, and fabric side edge extensions attached to the at least two side edges of the flexible sheet-like heating element; a layer of polymeric foam including a top surface, a bottom surface, an upper wall, a lower wall, and at least two side walls, the layer of polymeric foam positioned under the heater assembly; and a shell covering at least a portion of the heater assembly and the layer of polymeric foam, the shell comprising at least two sheets of flexible material, wherein a width of the flexible sheet-like heating element is wider than a width of the top surface of the layer of polymeric foam, wherein, when the heater assembly is wrapped around the top surface of the layer of polymeric foam, the at least two side edges of the flexible sheet-like heating element extend partially down the at least two side walls of the layer of polymeric foam and the conductive bus bars lie adjacent the at least two side walls of the layer of polymeric foam, and wherein the fabric side edge extensions are wrapped under and attached to the bottom surface of the layer of polymeric foam thereby securing the heater assembly to the layer of polymeric foam.

2. The heating pad of embodiment 1, wherein the heater assembly is adhesively connected to the top surface of the layer of polymeric foam over less than an entirety of the top surface of the layer of polymeric foam.

3. The heating pad of embodiment 1 or 2, wherein the heater assembly is adhesively connected to the top surface of the layer of polymeric foam at a location of the top surface of the layer of polymeric foam corresponding to an area of the heating pad that is configured to bend as a result of bending a surgical table into a sitting position.

4. The heating pad of embodiment 1, 2 or 3, wherein the heater assembly is not adhesively connected to the at least two side walls of the layer of polymeric foam.

5. The heating pad of embodiment 1, 2, 3, or 4, wherein a layer of foam material is bonded to the top surface of the heater assembly to form an unbonded friction connection between the layer of foam and the shell.

6. The heating pad of embodiment 1, 2, 3, 4, or 5, wherein the fabric side edge extensions of the heater assembly include vertical slits extending to and including the fabric side edge extensions that are attached to the bottom surface of the layer of polymeric foam, and wherein the vertical slits are at a location corresponding to an area of the heating pad that is configured to bend as a result of bending a surgical table into a sitting position.

7. The heating pad of embodiment 1, 2, 3, 4, 5, or 6, wherein the heater assembly includes at least one layer of polymeric oxygen barrier film attached to and covering at least one of the top surface and the bottom surface of the flexible sheet-like heating element.

8. The heating pad of embodiment 1, 2, 3, 4, 5, 6, or 7, wherein the heater assembly further includes a temperature control sensor attached to the flexible sheet-like heating element at a location configured to be in contact with a patient laying on the heating pad, wherein the heater assembly further includes a pressure sensor located adjacent the temperature control sensor to detect a weight of a patient laying on the heating pad, and wherein the pressure sensor is configured to reduce or turn off electrical power to the flexible sheet-like heating element when the weight of the patient has not been detected by the pressure sensor for a preset period of time.

9. The heating pad of embodiment 1, 2, 3, 4, 5, 6, 7, or 8, wherein the fabric lower edge extensions of the heater assembly are attached to the lower edge of the flexible sheet-like heating element, and wherein the fabric lower edge extensions are attached to the top surface, the lower wall and the bottom surface of the layer of polymeric foam at the perineal cutout and adjacent the perineal cutout to reinforce the perineal cutout against pressures applied during Trendelenburg securement.

10. An electric heating pad for warming a patient, the electric heating pad comprising a heated underbody support or heated mattress, the heated underbody support of heated mattress comprising: a heater assembly comprising: a flexible sheet-like heating element including a top surface, a bottom surface, an upper edge, a lower edge, and at least two side edges, conductive bus bars attached near each of the at least two side edges of the flexible sheet-like heating element, and fabric side edge extensions attached to the at least two side edges of the flexible sheet-like heating element; a layer of polymeric foam including a top surface, a bottom surface, an upper wall, a lower wall, and at least two side walls, the layer of polymeric foam positioned under the heater assembly, and a shell covering the heater assembly and the layer of polymeric foam, the shell comprising at least two sheets of flexible material, wherein, when the heater assembly is wrapped around the top surface of the layer of polymeric foam, the at least two side edges of the flexible sheet-like heating element and the conductive bus bars lie adjacent the at least two side walls of the layer of polymeric foam, and wherein the fabric side edge extensions are wrapped under and attached to the bottom surface of the layer of polymeric foam thereby securing the heater assembly to the layer of polymeric foam.

11. The heating pad of embodiment 10, wherein a width of the flexible sheet-like heating element is wider than a width of the top surface of the layer of polymeric foam, and wherein, when the heater assembly is wrapped around the top surface of the layer of polymeric foam, the at least two side edges of the flexible sheet-like heating element extend partially down the at least two side walls of the layer of polymeric foam and the conductive bus bars lie adjacent the at least two side walls of the layer of polymeric foam.

12. The heating pad of embodiment 10 or 11, wherein the heater assembly is adhesively connected to the top surface of the layer of polymeric foam over less than an entirety of the top surface of the layer of polymeric foam.

13. The heating pad of embodiment 10, 11, or 12, wherein the heater assembly is adhesively connected to the top surface of the layer of polymeric foam at a location of the top surface of the layer of polymeric foam corresponding to an area of the heating pad that is configured to bend as a result of bending a surgical table into a sitting position.

14. The heating pad of embodiment 10, 11, 12, or 13, wherein the heater assembly is not adhesively connected to the at least two side walls of the layer of polymeric foam.

15. The heating pad of embodiment 10, 11, 12, 13, or 14, wherein the fabric side edge extensions of the heater assembly include vertical slits extending to and including the fabric side edge extensions that are attached to the bottom surface of the layer of polymeric foam, and wherein the vertical slits are at a location corresponding to an area of the heating pad that is configured to bend as a result of bending a surgical table into a sitting position.

16. The heating pad of embodiment 10, 11, 12, 13, 14, or 15, wherein a layer of foam material is bonded to the top surface of the heater assembly to form an unbonded friction connection between the layer of foam and the shell.

17. The heating pad of embodiment 10, 11, 12, 13, 14, 15, or 16, wherein the heater assembly further includes a temperature control sensor attached to the flexible sheet-like heating element at a location configured to be in contact with a patient laying on the heating pad, wherein the heater assembly further includes a pressure sensor located adjacent the temperature control sensor to detect a weight of a patient laying on the heating pad, and wherein the pressure sensor is configured to reduce or turn off electrical power to the flexible sheet-like heating element when the weight of the patient has not been detected by the pressure sensor for a preset period of time.

18. The heating pad of embodiment 10, 11, 12, 13, 14, 15, 16, or 17, wherein the fabric lower edge extensions of the heater assembly are attached to the lower edge of the flexible sheet-like heating element, and wherein the fabric lower edge extensions are attached to the top surface, the lower wall and the bottom surface of the layer of polymeric foam at the perineal cutout and adjacent the perineal cutout to reinforce the perineal cutout against pressures applied during Trendelenburg securement.

19. An electric heating pad for warming a patient, the electric heating pad comprising a heated underbody support or heated mattress, the heated underbody support or heated mattress comprising: a heater assembly comprising: a flexible sheet-like heating element including a top surface, a bottom surface, an upper edge, a lower edge, and at least two side edges, conductive bus bars respectively attached near each of the at least two side edges of the flexible sheet-like heating element, a temperature control sensor attached to the flexible sheet-like heating element at a location configured to be in contact with a patient laying on the electric heating pad, a pressure sensor located adjacent the temperature control sensor to detect a weight of a patient laying on the electric heating pad, and fabric side edge extensions attached to the at least two side edges of the flexible sheet-like heating element; a layer of polymeric foam including a top surface, a bottom surface, an upper wall, a lower wall, and at least two side walls, the layer of polymeric foam positioned under the heater assembly; and a shell covering the heater assembly and the layer of polymeric foam, the shell comprising at least two sheets of flexible material, wherein, when the heater assembly is wrapped around the top surface of the layer of polymeric foam, the at least two side edges of the flexible sheet-like heating element and the conductive bus bars lie adjacent the at least two side walls of the layer of polymeric foam, wherein the fabric side edge extensions are wrapped under and attached to the bottom surface of the layer of polymeric foam thereby securing the heater assembly to the layer of polymeric foam, and wherein the pressure sensor is configured to reduce or turn off electrical power to the flexible sheet-like heating element when the weight of the patient has not been detected by the pressure sensor for a preset period of time.

20. The heating pad of embodiment 19, wherein the heater assembly is adhesively connected to the top surface of the layer of polymeric foam over less than an entirety of the top surface of the layer of polymeric foam.

21. The heating pad of embodiment 19 or 20, wherein the heater assembly is not adhesively connected to the at least two side walls of the layer of polymeric foam.

22. The heating pad of embodiment 19, 20, or 21, wherein the heater assembly includes at least one layer of polymeric oxygen barrier film attached to and covering at least one of the top surface and the bottom surface of the flexible sheet-like heating element.

23. The heating pad of embodiment 19, 20, 21, or 22, wherein the fabric lower edge extensions of the heater assembly are attached to the lower edge of the flexible sheet-like heating element, and wherein the fabric lower edge extensions are attached to the top surface, the lower wall and the bottom surface of the layer of polymeric foam at the perineal cutout and adjacent the perineal cutout to reinforce the perineal cutout against pressures applied during Trendelenburg securement.

24. An electric heating pad for warming a patient, the electric heating pad comprising a heated underbody support or heated mattress, the hated underbody support or heated mattress comprising: a heater assembly comprising: a flexible sheet-like heating element including a top surface, a bottom surface, an upper edge, a lower edge, and at least two side edges, conductive bus bars respectively attached near each of the at least two side edges of the flexible sheet-like heating element, fabric side edge extensions attached to the at least two side edges of the flexible sheet-like heating element, and a fabric lower edge extension attached to the lower edge of the flexible sheet-like heating element; a layer of polymeric foam including a top surface, a bottom surface, an upper wall, a lower wall, at least two side walls, and a perineal cutout in the lower wall, the layer of polymeric foam positioned under the heater assembly; and a shell covering the heater assembly and the layer of polymeric foam, the shell comprising at least two sheets of flexible material, wherein, when the heater assembly is wrapped around the top surface of the layer of polymeric foam, the at least two side edges of the flexible sheet-like heating element and the conductive bus bars lie adjacent the at least two side walls of the layer of polymeric foam, wherein the fabric side edge extensions are wrapped under and attached to the bottom surface of the layer of polymeric foam thereby securing the heater assembly to the layer of polymeric foam, and wherein the fabric lower edge extension, attached to the lower edge of the flexible sheet-like heating element, is attached to the top surface, the lower wall and the bottom surface of the layer of polymeric foam at the perineal cutout and adjacent the perineal cutout to reinforce the perineal cutout against pressures applied during Trendelenburg securement.

25. The heating pad of embodiment 24, wherein the heater assembly is adhesively connected to the top surface of the layer of polymeric foam over less than an entirety of the top surface of the layer of polymeric foam.

26. The heating pad of embodiment 24 or 25, wherein the heater assembly is not adhesively connected to the at least two side walls of the layer of polymeric foam.

27. The heating pad of embodiment 24, 25, or 26, wherein a layer of foam material is bonded to the top surface of the heater assembly to form an unbonded friction connection between the layer of foam and the shell.

28. The heating pad of embodiment 24, 25, 26, or 27, wherein the heater assembly further includes a temperature control sensor attached to the flexible sheet-like heating element at a location configured to be in contact with a patient laying on the heating pad, wherein the heater assembly further includes a pressure sensor located adjacent the temperature control sensor to detect a weight of a patient laying on the heating pad, and wherein the pressure sensor is configured to reduce or turn off electrical power to the flexible sheet-like heating element when the weight of the patient has not been detected by the pressure sensor for a preset period of time.

29. The heating pad of embodiment 24, 25, 26, 27, or 28, wherein the fabric side edge extensions of the heater assembly include vertical slits extending to and including the fabric side edge extensions that are attached to the bottom surface of the layer of polymeric foam, and wherein the vertical slits are at a location corresponding to an area of the heating pad that is configured to bend as a result of bending a surgical table into a sitting position.

30. The heating pad of embodiment 24, 25, 26, 27, 28, or 29, wherein the fabric lower edge extensions of the heater assembly are attached to the lower edge of the flexible sheet-like heating element, and wherein the fabric lower edge extensions are attached to the top surface, the lower wall and the bottom surface of the layer of polymeric foam at the perineal cutout and adjacent the perineal cutout to reinforce the perineal cutout against pressures applied during Trendelenburg securement.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 3A is a top plan view of a heating element assembly, according to some embodiments of the present invention, which may be incorporated in the blanket or pad shown in FIG. 1.

FIG. 3B is a section view of the temperature sensor assembly of FIG. 3A.

FIG. 11 is a cross sectional view of a heated mattress overlay or pad in accordance with embodiments of the invention.

FIG. 12 is a cross sectional view of a heated mattress overlay or pad in accordance with embodiments of the invention.

FIG. 13 is a cross sectional view of a heated mattress overlay or pad in accordance with embodiments of the invention.

FIG. 14 is a cross sectional view of a heated mattress overlay or pad with partial thickness cuts or channels in the foam layer in accordance with embodiments of the invention.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized. The term 'blanket', used to describe embodiments of the present invention, may be considered to encompass heating blankets and pads, and vice-versa. Pads may also be referred to as underbody support systems or mattresses. In other words, features of the invention are applicable to both blankets and pads, regardless of whether a feature is described in a particular embodiment with regard to a blanket, a pad or mattress (e.g., including mattress overlays and underbody supports).

Figure 1:
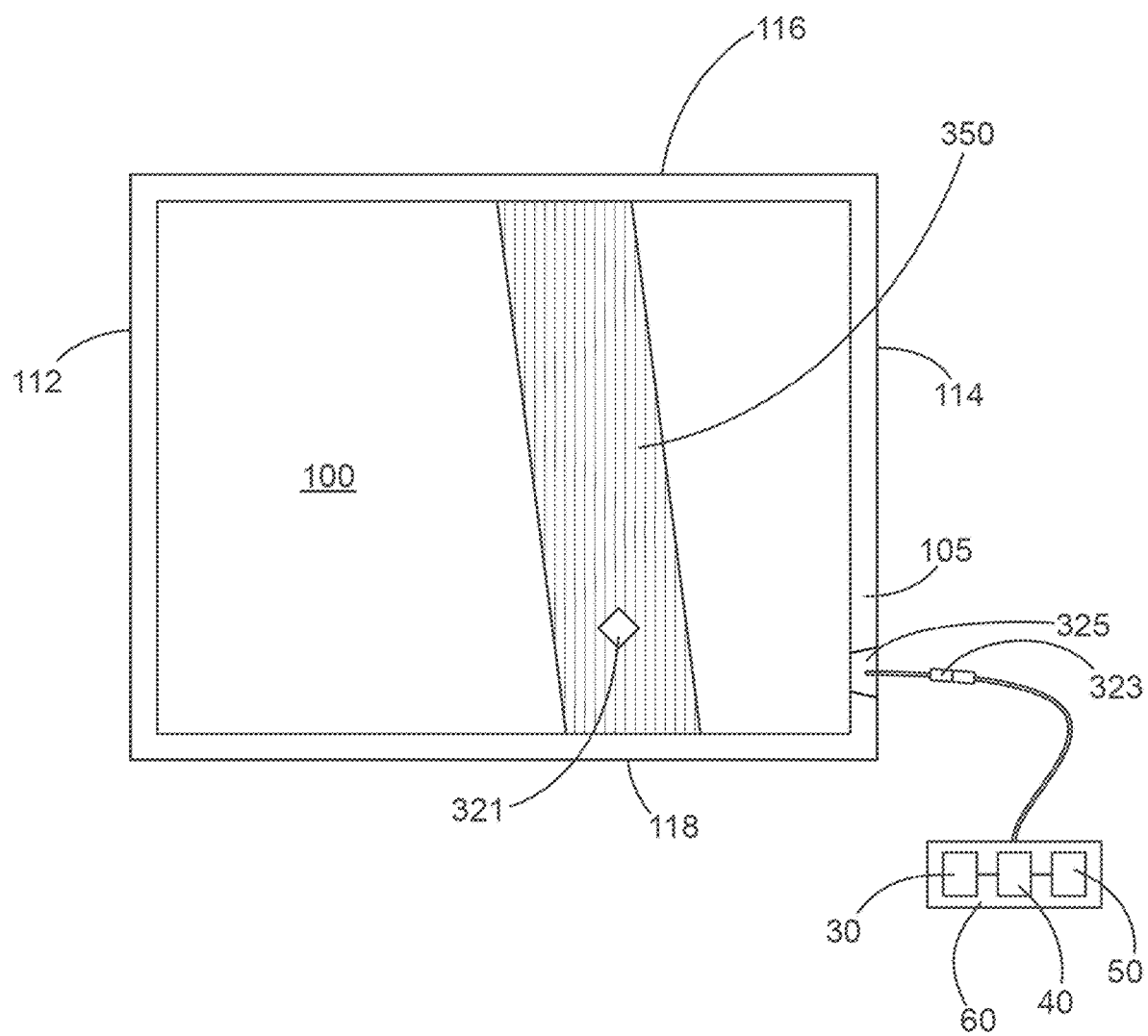
FIG. 1 is a top plan view of a heating blanket or pad, according to some embodiments of the present invention.

FIG. 1 shows a heating blanket or pad 100 according to some embodiments of the present invention. As shown, the heating blanket or pad 100 is generally rectangular. Embodiments of the present invention can be used in connection with a wide variety of heating blankets and pads. For example, in some cases, the heating blanket or pad 100 may be a blanket sized and shaped for the upper body or upper body limb (e.g., a wrap-around blanket), or a blanket sized and shaped for the lower body or lower body limb. In some cases the heating blanket or pad 100 can be used in conjunction with a disposable cover. In other embodiments, the heating blanket or pad 100 may be a mattress overlay or underbody support mattress.

The heating blanket or pad 100 of FIG. 1 includes a shell 105 that can be durable and waterproof. As shown, a portion of the shell 105 is cut away, revealing a heating element assembly 350. The heating element assembly 350 is generally covered by the shell 105 and can extend within the shell 105 between edge 112 and edge 114 and between edge 116 and edge 118. An electrical connector housing 325 and a corresponding connector plug 323 can be coupled to the shell 105, thereby enabling access to a temperature sensor assembly such as those discussed below.

The shell 105 can protect and isolate the heating element assembly 350 from an external environment of heating blanket 100. The shell 105 can include a water-resistant material layer that can form a substantially hermetic seal around the heating element assembly 350. The shell 105 can provide further protection to a patient disposed beneath heating blanket or pad 100 against electrical shock hazards. According to preferred embodiments of the present invention, shell 105 is waterproof to prevent fluids (e.g., bodily fluids, IV fluids, cleaning fluids, etc.) from contacting the heating element assembly 350. In some preferred embodiments, shell 105 may further include an anti-microbial element (e.g., a SILVERion™ antimicrobial fabric available from Domestic Fabrics Corporation or Ultra-Fresh™ from Thomson Research Associates).

According to an illustrative embodiment of the present invention, shell 105 comprises polyvinyl chloride (PVC) or urethane (TPU) to facilitate an RF weld to bond the sheets. It should be noted that, according to some embodiments of the present invention, a covering for heating element assemblies may be removable and, thus, include a reversible closure facilitating removal of a heating element assembly 350 therefrom and insertion of the same or another heating element assembly 350 therein. In some embodiments, shell 105 comprises a PVC or TPU film of sufficient thickness to provide the necessary strength. In some such embodiments, the edge seals can be softer. In some examples, the shell can be made of a layer of PVC film attached (e.g., laminated) onto a layer of fabric, sometimes referred to as Naugahyde. Other suitable shell materials that are flexible and waterproof can be utilized.

In some embodiments, one or more layers may be positioned between the heating element assembly 350 and the shell 105. For example, in some embodiments, [a layer of thermally insulating material] (e.g., polymeric foam or high-loft fibrous non-woven material) can be included in one or more locations.

In some instances a layer of thermally insulating material can be positioned to make sure that a maximal amount of heat being generated by the heating element assembly 350 is transferred to the patient. In such instances, a layer of thermally insulating material can help insulate the heating element assembly 350 from the environment and provide a more uniform temperature distribution. The layer of thermally insulating material can be positioned between the heating element assembly 350 and the surface of the shell 105 that does not contact the patient. In this way, a maximal amount of heat being generated by the heating element assembly 350 can be transferred to the patient and not to the surrounding environment.

In some instances a layer of thermally insulating material can be positioned to prevent caregivers from experiencing unwanted contact with activated heating blankets or pads. Other layers (e.g., an electrically insulating layer similar to those discussed elsewhere herein) can be positioned between the heating element assembly 350 and the shell 105.

Figure 2A:
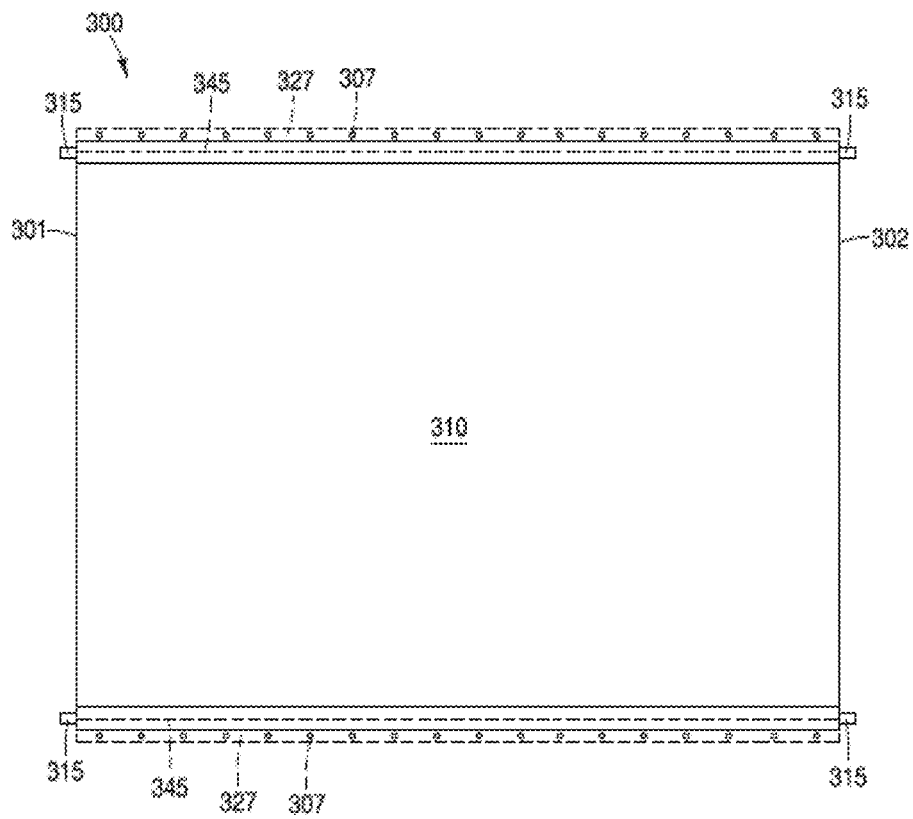
FIG. 2A is a plan view of a flexible heating blanket or pad subassembly for a heating blanket or pad, according to some embodiments of the present invention.
Figure 2B:
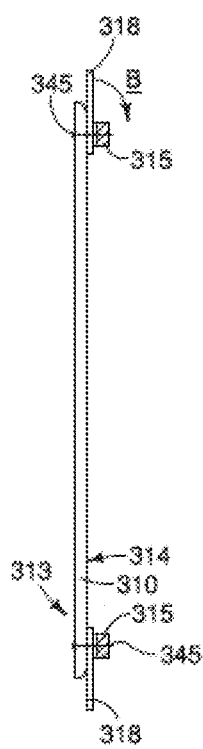
FIG. 2B is an end view of some embodiments of the subassembly shown in FIG. 2A.

FIGS. 2A-2B show an illustrative heating blanket or pad subassembly 300 that can be incorporated into heating element assemblies in some embodiments of the present invention (e.g., heating element assembly 350 of FIG. 1). Referring again to FIGS. 2A-2B, in many embodiments, the heating blanket or pad subassembly 300 is flexible. The heating blanket or pad subassembly 300 can include a flexible sheet-like heating element 310, or heater, which can include a first side edge 301 and a second side edge 302. According to preferred embodiments of the present invention, heating element 310 comprises a conductive fabric or a fabric incorporating closely spaced conductive elements such that heating element 310 has a substantially uniform watt density output, preferably less than approximately 0.5 watts/sq. inch, and more preferably between approximately 0.2 and approximately 0.4 watts/sq. inch, across a surface area, of one or both sides 313, 314 (FIG. 2B).

Some examples of conductive fabrics which may be employed by embodiments of the present invention include, without limitation, carbon fiber fabrics, fabrics made from carbonized fibers, conductive films, or woven or non-woven non-conductive fabric or film substrates coated with a conductive material, for example, polypyrrole, carbonized ink, or metalized ink. In many embodiments, the conductive fabric is a polymeric fabric coated with a conductive polymeric material such as polypyrrole. In addition, the flexible heating element 310 may be made from a matrix of electrically resistant wire or metal traces attached to a fibrous or film material layer.

In some embodiments, in contrast to non-stretchable conductive film heaters, where a carbon (or other conductive material) impregnated plastic film is extruded onto or bonded onto a base layer such as a fabric base layer, the preferred heating element 310 material has a conductive or semi-conductive material coated onto the individual threads or fibers of the carrier fibers prior to weaving or knitting into a fabric. This maintains the natural flexibility and stretchability of the fabric rather than turning the fabric into a non-stretchable fiber reinforced film.

In some embodiments, the conductive or semi-conductive coating comprises a polymer and is bound as a layer surrounding the individual threads or fibers by a process of polymerization. Polymerization results in a very secure bond. The flexible coating on each individual thread or fiber preferably does not crack, fracture or delaminate during flexion. Polymerization of these conductive or semi-conductive materials onto individual fibers of the carrier fabric is a preferable process for producing a durable, flexible and stretchable heater assembly 300. Semi-conductive polymer coatings such as polypyrrole are preferred for this invention, however, other coating processes are anticipated and conductive coatings that use carbon or metal as the conductive material are also anticipated In some embodiments, the conductive material may be stretchable in at least one direction or, alternatively, in at least two directions. One way to create a stretchable fabric heating element (e.g., 310) is to coat a conductive material onto individual threads or fibers of a carrier fabric which may be a non-conductive material. The threads or fibers may be woven or knitted, for example, into a stretchable fabric. Other examples of conductive fabrics which may be employed include, without limitation, carbon fiber fabrics, fabrics made from carbonized fibers, and woven or non-woven substrates coated with a conductive material, for example, polypyrrole, carbonized ink, or metalized ink.

The conductive material may be applied to the fibers or threads before they are woven or knit into a fabric. In this way, the coated threads can move and slide relative to each other as the fabric is stretched, and can return to their original orientation when the stretching is stopped such that the fabric can return to its original shape. Alternatively, the conductive materials that coat the individual fibers in the fabric may be applied after the fabric is woven or knit using a dipping, spraying, coating or polymerization process or combinations thereof. A conductive polymer can be selected that coats to the individual threads without bonding them together such that the threads remain able to slide relative to each other.

The stretchable fabric heating element (e.g., 310) is able to deform in response to a focal pressure applied to the surface of the heater fabric, into a smooth 3-dimensional compound curve without wrinkling or folding. A smooth compound curve cannot be formed out of non-stretchable fabrics or films. The stretchable fabric heating element may also exhibit elastic properties that allow it to revert to its original planar shape when the deforming pressure is relieved. The fabric heating element can be provided with appropriate tensile properties such that the amount of stretch, or strain, required to prevent hammocking and allow accommodation of the patient into the heated mattress or mattress overlay does not result in stresses that exceed the elastic limit of the material. In some embodiments, for example, an increase in the width of a 20 inch wide mattress or mattress overlay of approximately one inch during stretching achieves the desired goals without exceeding the elastic limit of the stretchable fabric heating element or introducing permanent plastic deformation.

FIG. 2A further illustrates subassembly 300 including two bus bars 315 coupled to heating element 310 for powering heating element 310. Each bus bar 315 is shown extending between first and second side edges 301, 302. With reference to FIG. 2B, according to some embodiments, bus bars 315 are coupled to heating element 310 by a stitched coupling 345 (e.g., formed with conductive thread such as silver-coated polyester or nylon thread (Marktek Inc., Chesterfield, MO)).

As shown, insulation is provided between the bus bars 315 and the heating element 310. FIG. 2B illustrates subassembly 300 wherein insulating members 318 (e.g., fiberglass material strips having an optional PTFE coating and a thickness of approximately 0.003 inch) extend between bus bars 315 and heating element 310 at each stitched coupling 345, so that electrical contact points between bars 315 and heating element 310 are solely defined by the conductive thread of stitched couplings 345. Alternatively, the electrical insulation material layer could be made of polymeric film, a polymeric film reinforced with a fibrous material, a cellulose material, a glass fibrous material, rubber sheeting, polymeric or rubber coated fabric or woven materials or any other suitable electrically insulating material.

Each of the conductive thread stitches of coupling 345 can maintain a stable and constant contact with bus bar 315 on one side and heating element 310 on the other side of insulating member 318. The stitches produce a stable contact in the face of any degree of flexion, so that the potential problem of intermittent contact between bus bar 315 and heating element 310 (that could arise for the embodiment shown in FIG. 2B, where bus bar 315 is in physical contact with heating element 310) can be avoided. The stitches (e.g., 345) are the only electrical connection between bus bar 315 and heating element 310, but, since the conductive thread has a much lower electrical resistance than the conductive fabric of heating element 310, the thread does not heat under normal conditions.

In addition to heating blanket applications described herein, such a design for providing for a uniform and stable conductive interface between a bus bar and a conductive fabric heating element material can be used in other applications. For example, such a design can improve the conductive interface between a bus bar or electrode and a conductive fabric in non-flexible heating elements, in electronic shielding, in radar shielding and other applications of conductive fabrics.

In some preferred embodiments, coupling 345 includes two or more rows of stitches for added security and stability. However, due to the flexible nature of blanket or pad subassembly 300, the thread of stitched couplings 345 may undergo significant stresses. These stresses, over time and with multiple uses of a blanket or pad containing subassembly 300, could lead to one or more fractures along the length of stitched coupling 345. Such a fracture, in other designs, could also result in intermittent contact points, between bus bar 315 and heating element 310 that could lead to a thermal breakdown of heating element 310 along bus bar 315. But, if such a fracture were to occur in the embodiment of FIG. 2B, insulating member 318 may prevent a thermal breakdown of heating element 310, so that only the conductive thread of stitched coupling 345 melts down along bus bar 315. According to some preferred embodiments, more than two rows of stitches are applied to each bus bar 315 for added safety and stability of the bus bar 315/heating element 310 interface.

Alternative threads or yarns employed by embodiments of the present invention may be made of other polymeric or natural fibers coated with other electrically conductive materials. In addition, nickel, gold, platinum and various conductive polymers can be used to make conductive threads. Metal threads such as stainless steel, copper or nickel could also be used for this application.

According to an exemplary embodiment, bus bars 315 are comprised of flattened tubes of braided wires, such as are known to those skilled in the art (e.g., a flat braided silver coated copper wire) and may thus accommodate the thread extending therethrough, passing through openings between the braided wires thereof. In addition such bus bars 315 are flexible to enhance the flexibility of blanket or pad subassembly 300. According to alternate embodiments, bus bars 315 can be a conductive foil or wire, flattened braided wires not formed in tubes, an embroidery of conductive thread, or a printing of conductive ink. Preferably, bus bars 315 are each a flat braided silver-coated copper wire material, since a silver coating has shown superior durability with repeated flexion, as compared to tin-coated wire, for example, and may be less susceptible to oxidative interaction with a polypyrrole coating of heating element 310 according to an embodiment described below. Additionally, an oxidative potential, related to dissimilar metals in contact with one another is reduced if a silver-coated thread is used for stitched coupling 345 of a silver-coated bus bar 315.

According to an exemplary embodiment, a conductive fabric comprising heating element 310 comprises a non-woven polyester having a basis weight of approximately 170 g/m2 and being 100% coated with polypyrrole (available from Eeonyx Inc., Pinole, CA). The coated fabric has an average resistance (e.g., determined with a four point probe measurement) of approximately 15 ohms per square inch. This average resistance is suitable to produce the preferred watt density of 0.2 to 0.4 watts/sq. in. for surface areas of heating element 310 having a width, between bus bars 315, in the neighborhood of about 19 to 28 inches, when powered at about 48 volts. In some embodiments, the basis weight of the non-woven polyester may be chosen in the range of approximately 80-180 g/m2. However, other basis weights may be engineered to operate adequately are therefore within the scope of embodiments of the invention.

A resistance of such a conductive fabric may be tailored for different widths between bus bars 315 (wider requiring a lower resistance and narrower requiring a higher resistance) by increasing or decreasing a surface area of the fabric that can receive the conductive coating. In some instances, this can be achieved by increasing or decreasing the basis weight of the nonwoven. Resistance over the surface area of the conductive fabrics (e.g., 310) is generally uniform in many embodiments of the present invention. However, the resistance over different portions of the surface area of conductive fabrics such as these may vary (e.g., due to (a) variation in a thickness of a conductive coating, (b) variation within the conductive coating itself, (c) variation in effective surface area of the substrate which is available to receive the conductive coating, or (d) variation in the density of the substrate itself). Local surface resistance across a heating element, for example heating element 310, is directly related to heat generation according to the following relationship:

$$Q(\text{Joules}) = I^2(\text{Amps}) \times R(\text{Ohms})$$

Variability in resistance thus translates into variability in heat generation, which can ultimately manifest as a variation in temperature.

According to preferred embodiments of the present invention, which are employed to warm patients undergoing surgery, precise temperature control is desirable. Means for determining heating element 310 temperatures, which average out temperature variability caused by resistance variability across a surface of the heating element 310, are described below in conjunction with FIG. 3A.

Referring again to FIGS. 2A-2B, the flexibility of blanket or pad subassembly 300 can allow blanket or pad subassembly 300 to conform to the contours of a body (e.g., all or a portion of a patient undergoing surgery). This flexibility can be provided primarily by flexible heating element 310 and can be optionally enhanced by the incorporation of flexible bus bars 315. Conforming to the contours of a patient's body is preferable to simply bridging across high spots of the body. Such conformance may optimize a conductive heat transfer from heating element 310 to a surface of the body.

The uniform watt-density output across the surface areas of preferred embodiments of heating element 310 translates into generally uniform heating of the surface areas, but not necessarily a uniform temperature. For example, at locations of heating element 310 which are in conductive contact with a body acting as a heat sink, the heat is efficiently drawn away from heating element 310 and into the body (e.g., by blood flow). At the same time, at those locations where heating element 310 does not come into conductive contact with the patient's body, an insulating air gap exists between the body and those portions, so that the heat is not drawn off those portions as easily. Therefore, those portions of heating element 310 not in conductive contact with the body will gain in temperature, since heat is not transferred as efficiently from these portions as from those in conductive contact with the body. The 'non-contacting' portions will reach a higher equilibrium temperature than that of the 'contacting' portions, when the radiant and convective heat loss equal the constant heat production through heating element 310. Since the heat generation is generally uniform, the heat flux to the patient will also be generally uniform. However, at the non-contacting locations, the temperature is higher to achieve the same flux as the contacting portions. Some of the extra heat from the higher temperatures at the non-contacting portions can therefore be dissipated out the back of the blanket or pad 100 instead of into the patient.

Although radiant and convective heat transfer are more efficient at higher heater temperatures, the laws of thermodynamics dictate that as long as there is a uniform watt-density of heat production, even at the higher temperature, the radiant and convective heat transfer from a blanket or pad of this construction will result in a generally uniform heat flux from the blanket or pad. Therefore, by controlling the 'contacting' portions to a safe temperature (e.g., via a temperature sensor assembly 321 coupled to heating element 310 in a location where heating element 310 will be in conductive contact with the body), the 'non-contacting' portions, will also be operating at a safe temperature because of the less efficient radiant and convective heat transfer.

According to preferred embodiments, heating element 310 comprises a conductive fabric having a relatively small thermal mass. When a portion of such a heating element that is operating at the higher temperature is touched, suddenly converting a 'non-contacting' portion into a 'contacting' portion, that portion will cool almost instantly to the lower operating temperature.

FIGS. 3A-3B show a heating element assembly 350 similar to the heating element assembly 350 of FIG. 1. Referring again to FIGS. 3A-3B, the heating element assembly 350 can include a temperature sensor assembly 321. As shown, the temperature sensor assembly 321 is coupled to heating element 310 at a location where heating element 310 would come into conductive contact with the patient. This can assist in maintaining a safe temperature distribution across heating element 310. The more constant the temperature information, the more the temperature controller can rely on it in controlling the heater (e.g., heating element 310, heating element assembly 350) temperature. In some embodiments, the temperature sensor assembly 321 can even be provided separately from the heating blanket or pad.

According to embodiments of the present invention, zones of heating element 310 may be differentiated according to whether or not portions of heating element 310 are in conductive contact with a body (e.g., a patient undergoing surgery). In some embodiments, the threshold temperature is between 37 and 43° C. In one particular embodiment, the threshold temperature is 43° C. A temperature of 43° C. has been shown to provide beneficial warming to a patient without providing excessive heat. In the case of conductive heating, gentle external pressure may be applied to a heating blanket or pad 100 including heating element 310. Such pressure conforms heating element 310 into better conductive contact with the patient to improve heat transfer. However, if excessive pressure is applied, the blood flow to that skin may be reduced at the same time that the heat transfer is improved and this combination of heat and pressure to the skin can be dangerous. It is well known that patients with poor perfusion should not have prolonged contact with temperatures in excess of approximately 42° C. Several studies show 42° C. to be the highest skin temperature that cannot cause thermal damage to normally perfused skin, even with prolonged exposure. (Stoll & Greene, Relationship Between Pain and Tissue Damage Due to Thermal Radiation. J. Applied Physiology 14(3):373-382. 1959; and Moritz and Henriques, Studies of Thermal Injury: The Relative Importance of Time and Surface Temperature in the Causation of Cutaneous Burns. Am. J. Pathology 23:695-720, 1947). Thus, according to certain embodiments of the present invention, the portion of heating element 310 that is in conductive contact with the patient is controlled to approximately 43° C. in order to achieve a temperature of about 41-42° C. on a surface of a heating blanket or pad cover (e.g., shell 105 of FIG. 1) that surrounds heating element 310. In the case of a heated mattress, the temperature may be limited, for instance, to a maximum of 40° C. in order to avoid the combination of excessive heat and pressure on the skin.

FIG. 3B illustrates the temperature sensor assembly 321 assembled on side 314 of the heating element 310. As shown, the heating element 310 is overlaid on both sides 313, 314 with an electrically insulating layer 330. The electrically insulating layer 330 is preferably formed of a flexible non-woven very low loft fibrous material (e.g., 1.5 ounces-per-square-yard nylon), which is preferably laminated to sides 313, 314 with a hotmelt laminating adhesive. In some embodiments, the adhesive is applied over the entire interfaces between insulating layer 330 and heating element 310. Other examples of suitable materials for insulating layer 330 include, without limitation, polymeric foam, a woven fabric, such as cotton or fiberglass, and a relatively thin plastic film, cotton, and a non-flammable material, such as fiberglass or treated cotton. According to preferred embodiments, overlaid insulating layers 330 prevent electrical shorting of one portion of heating element 310 with another portion of heating element 310 if the heating element 310 is folded over onto itself. Many such embodiments prevent electrical shorting without compromising the flexibility of heating assembly 350. Heating element assembly 350 may be powered by a relatively low voltage (approximately 48V). Insulating layers 330 may even be porous in nature to further maintain the desired flexibility of assembly 350.

As shown in FIG. 3A, an assembly of leads 305, 306 and junctions 355 can connect the bus bars 315 and the temperature sensor assembly 321 to an electrical connector housing 325. Leads 305 couple the connector housing 325 to bus bars 315 at junctions 355. Lead 306 couples the temperature sensor assembly 321 to the connector housing 325. In many embodiments, leads 305, 306 extend over any insulating layer (e.g., 330 in FIG. 3B) and into the electrical connector housing 325. As is noted above (see discussion in connection with FIG. 1) and discussed in greater detail below (see discussion in connection with FIG. 4A), electrical connector housing 325 can contain a connector plug 323.

Returning now to FIG. 3B, the illustrative temperature sensor assembly 321 will be described in greater detail. The temperature sensor assembly 321 can include a temperature sensor 351 (e.g., a surface mount chip thermistor (such as a Panasonic ERT-J1VG103FA: 10K, 1% chip thermistor)) soldered to an etched metal foil. In many embodiments, a substrate 331 (e.g., of polyimide (Kapton)) surrounds the temperature sensor 351. A heat spreader 332 (e.g., a copper or aluminum foil) can be mounted to an opposite side of substrate 331 (e.g., being bonded with a pressure sensitive adhesive). Substrate 331 can be relatively thin (e.g., about 0.0005-inch thick) so that heat transfer between heat spreader 332 and sensor is not significantly impeded.

In some embodiments, the temperature sensor 351 is positioned such that the regions surrounding sensor 351 will be in conductive contact with the body when a heating blanket or pad is placed over a body. As previously described, in many instances, it is desirable that a temperature of approximately 43° C. be maintained over a surface of heating element 310 which is in conductive contact with a non-dependent surface (upper surface) of the body of a patient undergoing surgery. An additional alternate embodiment is contemplated in which an array of temperature sensors are positioned over the surface of heating element 310, being spaced apart to collect temperature readings. In some such embodiments, the collected temperatures can be averaged to account for resistance variance. In some examples, it is advantageous to control the temperatures of a mattress, such as a heated mattress, that is in contact with the dependent (lower) surface of the body of a patient to a maximum of 40° C.

Figure 4A:
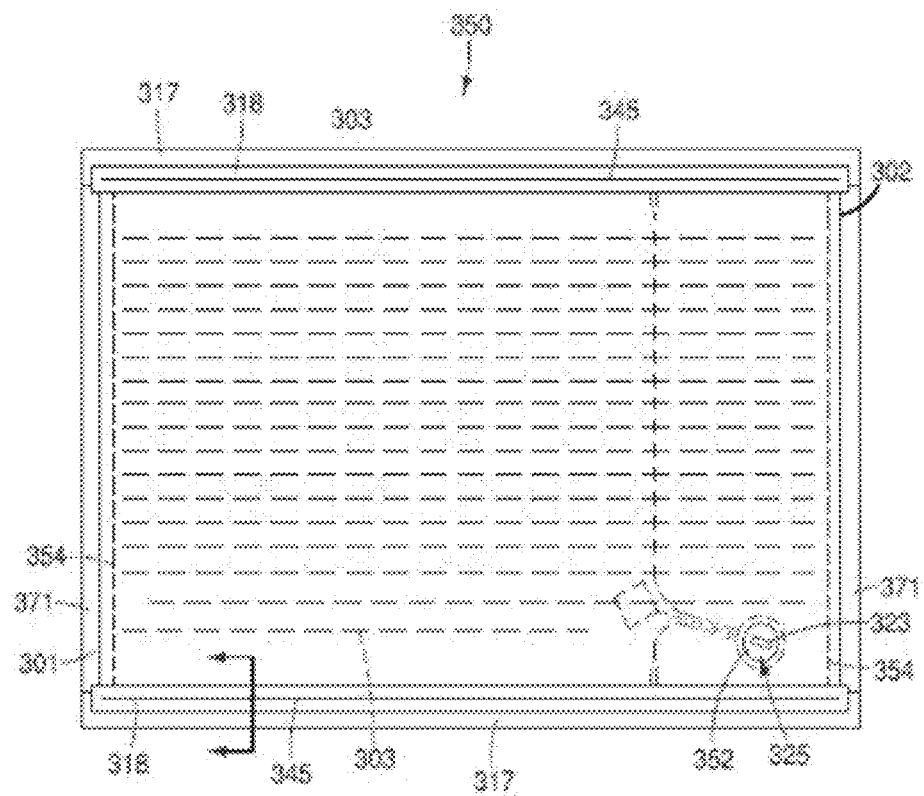
FIG. 4A is a top plan view of a heating element assembly, which may be incorporated in the blanket or pad shown in FIG. 1.
Figure 4B:
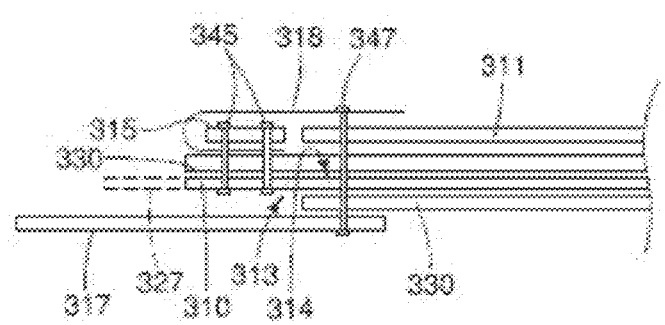
FIG. 4B is a cross-section view through section line 4B-4B of FIG. 4A.

FIGS. 4A-4B show a heating element assembly 350 that may be incorporated into a heating blanket or pad (e.g., heating blanket or pad 100 of FIG. 1). As shown, the heating element assembly 350 includes heating element 310 overlaid with electrical insulation 330 on both sides 313, 314 and a thermal insulation layer 311 extending over the top side 314 thereof (dashed lines show leads and sensor assembly beneath layer 311).

A heating blanket or pad may 100 include a layer of thermal insulation 311 extending over a top side (corresponding to side 314 of heating element 310 as shown in FIG. 2B) of heating assembly 350 as discussed above. According to the illustrated embodiment, layer 311 is inserted beneath a portion of each insulating member 318. The insulating members 318 have been folded over the respective bus bar 315 (e.g., as illustrated by arrow B in FIG. 2B), and then held in place by a respective row of non-conductive stitching 347 that extends through insulating member 318, layer 311 and heating element 310. Although not shown, it should be appreciated that layer 311 may further extend over bus bars 315. Although insulating layer 330 is shown extending beneath layer 311 on side 314 of heating element 310, according to alternate embodiments, layer 311 independently performs as a thermal and electrical insulation so that insulating layer 330 is not required on side 314 of heating element 310. FIG. 4A further illustrates, with longitudinally extending dashed lines, a plurality of optional slits 303 in layer 311, which may extend partially or completely through layer 311, in order to increase the flexibility of assembly 350. Such slits 303 are desirable if a thickness or density of layer 311 is such that it prevents the heating blanket or pad 100 from draping (e.g., curving, deforming) effectively about a patient. The optional slits 303 are preferably formed, for example, extending only partially through layer 311 starting from an upper surface thereof, to allow bending of the heating blanket or pad 100 about a patient and to prevent bending of the heating blanket or pad 100 in the opposition direction.

Returning now to FIG. 3A, to be referenced in conjunction with FIGS. 1 and 4A, connector housing 325 and connector plug 323 will be described in greater detail. According to certain embodiments, housing 325 is an injection molded thermoplastic (e.g., PVC or urethane) and may be coupled to assembly 350 by being stitched into place and sealed between the flexible sheets of the shell.

FIGS. 4A-4B further illustrate a pair of securing strips 317, each extending laterally from and alongside respective lateral portions of heating element 310, parallel to bus bars 315, and each coupled to side 313 of heating element 310 by the respective row of non-conductive stitching 347. Another pair of securing strips 371 is shown in FIG. 4A, each strip 371 extending longitudinally from and alongside respective side edges 301, 302 of heating element 310 and being coupled thereto by a respective row of non-conductive stitching 354. Strips 371 may extend over layer 311 or beneath heating element 310. As shown, strips 317 preferably extend over conductive stitching of stitched coupling 345 on side 313 of heating element 310. The strips 317 can provide a layer of insulation that can prevent shorting between portions of side 313 of heating element 310 if heating element 310 were to fold over on itself along rows of conductive stitching of stitched coupling 345 that couple bus bars 315 to heating element 310. In some embodiments, strips 317 may alternately extend over insulating member 318 on the opposite side of heating element 310. According to the illustrated embodiment, securing strips 317 and 371 are made of a polymer material (e.g., PVC or urethane). They may be heat sealed, RF sealed or ultrasonically sealed between the sheets of shell (105 of FIG. 1) in corresponding areas of the heat seal zone in order to secure heating element assembly 350 within a corresponding gap between the two sheets of shell (105 of FIG. 1). According to an alternate embodiment, for example, shown by dashed lines in FIGS. 2A and 4B, heating element 310 extends laterally out from each bus bar 315 to a securing edge 327, which may include one or more slots or holes 307 extending therethrough so that inner surfaces of sheets of shell (105 of FIG. 1) can contact one another to be sealed together and thereby hold edges 327.

The power source 50 and power type can be any type known in the art. In certain embodiments, the power source 50 supplies a straight-line DC voltage to the control system 41, and the control system 41 provides a pulse-width-modulated voltage (e.g., at a 75% duty cycle) to the heating element assembly 350. Of course, other duty cycles and/or voltage levels can be used based on the design of the blanket or pad 100 and its heating element in order to achieve a desired threshold temperature in a reasonable amount of time. Too high of voltage or duty cycle, while decreasing the time to reach the desired temperature threshold, may increase the amount of temperature overshoot before the control system 41 reduces or shuts off power. Moreover, in the case of temperature sensor (e.g., 321) failure, thermal runaway presents a greater concern with relatively higher voltage or duty cycle settings. Too low of a voltage or duty cycle may cause unreasonably long warm-up times.

As discussed above, warming blankets and pads in accordance with embodiments of the invention include or make use of a shell or covering, such as shell 105 shown in FIG. 1. Several embodiments of such shells will now be described in greater detail, although it should be understood that these embodiments are for illustrative purposes only.

Figure 5A:
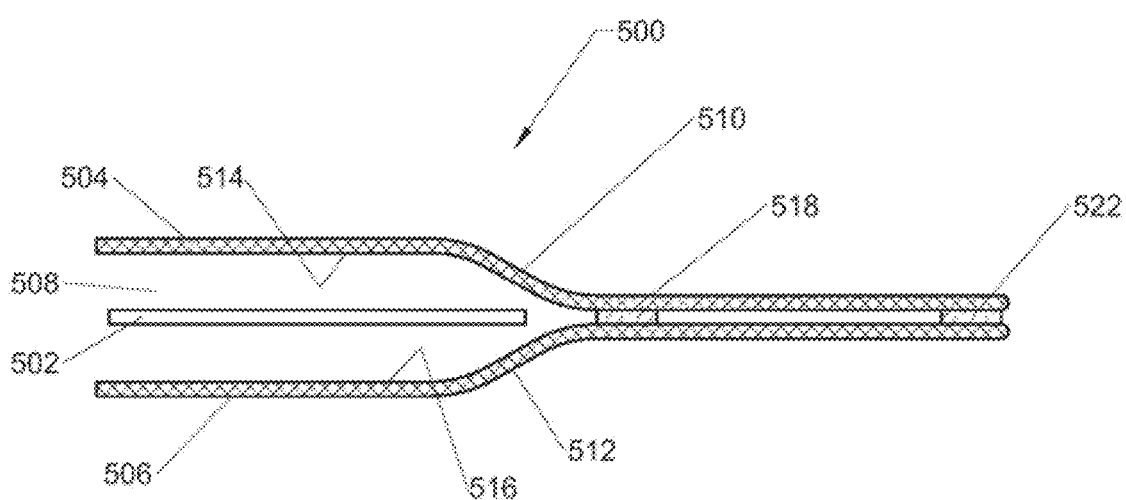
FIG. 5A is a cross-section of a shell containing a heating element according to some embodiments of the present invention.

FIG. 5A is a cross-section of a shell 500 containing a heating element 502 in accordance with some embodiments of the invention. The shell 500 can include a top sheet 504 and a bottom sheet 506 that are welded or coupled at one or more locations in order to define a pocket or pouch 508 that can enclose the heating element 502. Heating element 502 may include characteristics of heating element 310 or may be included in a heating element assembly such as 350. Any type of suitable weld may be used, such as heat welding (heat bonding), RF welding, ultrasonic welding, etc., depending on the type of materials used in sheets 504, 506. Each sheet 504 and 506 can comprise a flexible, substantially water-resistant material and include the ability to be welded together. As one of ordinary skill in the art would consider, sheets 504, 506 may be formed of two or more distinct sheets of material, including a single sheet of material folded over on itself or any other suitable construction. In some embodiments, the water-resistant material includes a single layer, and in some embodiments, the sheets 504, 506 are comprised of a laminate of two or more layers. For instance, in some embodiments one or both of sheets 504, 506 are comprised of a single layer of polyvinyl chloride (PVC) or urethane (TPU). In such embodiments where PVC or TPU is used, high frequency or RF welding (RF heat sealing) may be used to bond the sheets 504, 506 together. PVC or urethane sheets also provide a water-resistant material in order to protect the heating element 502 from fluids to which the heating blanket or pad 100 is exposed.

In some embodiments, one or both of sheets 504, 506 include respective strengthening layers 510, 512 that provide strength and color to the shell 500. For example, the strengthening layers 510, 512 can be a fibrous material such as woven nylon. It will be appreciated that other materials can also be used for this layer.

With further reference to FIG. 5A, sheets 504, 506 can each also include a second layer 514, 516 located along an inside surface of the sheets 504, 506. These second layers 514, 516 may in some embodiments provide a water-resistant layer in order to protect the heating element 502 from fluids to which the heating blanket or pad is exposed. For example, the second layers 514, 516 may be a polymeric film attached to the strengthening layer. In some embodiments, the second layers 514, 516 are preferably polymeric film layers that are a durable and made of a weldable material, such as urethane or vinyl, which can be laminated or extrusion coated on to the strengthening layers 510, 512 and the second layers 514, 516 may be welded together via heating bonding along the bonding points.

In some embodiments, one or both of sheets 504, 506 include a third layer laminated to their respective outer surfaces. The third layer, in some embodiments, is a polymeric layer, which may or may not be the same material as second layers 514, 516 in some embodiments. For example, the third layer may comprise a polymeric layer that can substantially seal one or both of the strengthening layers so that it cannot be substantially wetted. In some embodiments, the third layer may also be somewhat tacky so that it prevents the blanket from slipping when applied over a patient, or a patient from slipping when provided on a pad. The third layer may also comprise a material with the ability to limit and/or prevent iodine and cleaning solutions from staining the blanket or pad. Examples of materials that could serve this purpose include vinyl and silicone.

With further reference to FIG. 5A, top sheet 504 (e.g., first sheet) and bottom sheet 506 (e.g., bottom sheet) can be positioned on opposing sides of heating element 502 to envelope the heating element. Although descriptive terms "top" and "bottom" are used herein, it will be appreciated that in some embodiments, the sheets 504 and 506 may be identical and that either sheet may be referred to as "top" or "bottom", or "first" and second. Sheets 504 and 506 may be formed of a singular piece of material folded over on itself to provide the two sheets, or at least two sheets. Although sometimes referred to as a first sheet 504 and second sheet 506, the first and second sheets 504, 506 may be formed of a singular piece of material folded over on itself to provide the first sheet 504 and the second sheet 506. As shown in the embodiment of FIG. 5A, the sheets 504, 506 are positioned so that the weldable layers 514, 516 of each sheet oppose each other.

Figure 5B:
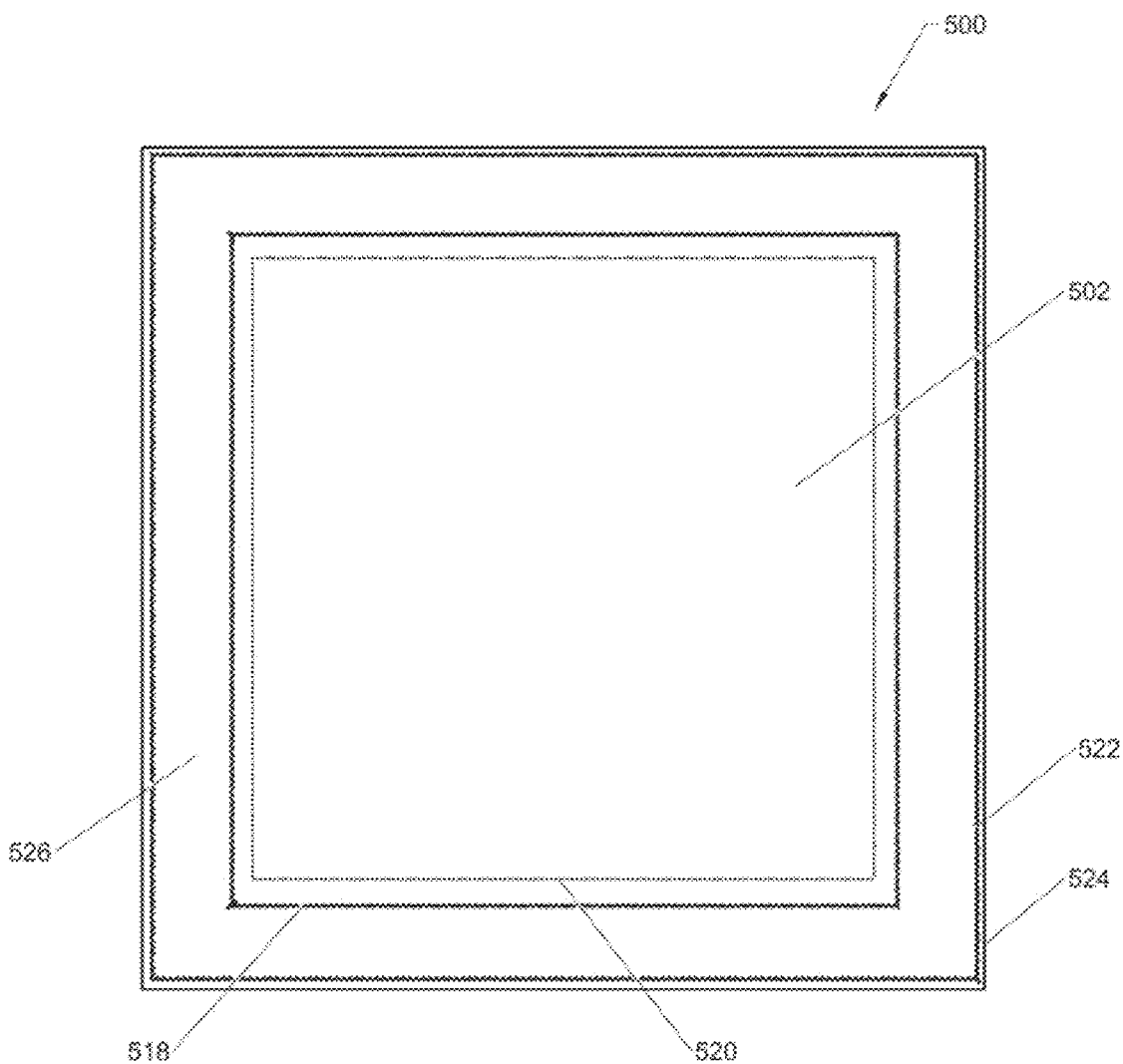
FIG. 5B is a top plan view of the shell of FIG. 5A.

FIG. 5B is a top plan view of the heating blanket or pad 500 depicted in FIG. 5A. In some embodiments, the sheets 504, 506 are sized to completely cover the heating element 502, and can extend beyond all edges (e.g., top, bottom, right and left side edges in FIG. 5B) of the heating element 502. In some embodiments, the heating element 502 is substantially hermetically sealed into the shell 500 formed by the two sheets 504, 506 (e.g., two or more distinct sheets or one sheet folded over on itself to form two sheets). As shown in the embodiment of FIGS. 5A and 5B, the sheets 504, 506 are coupled together along two welds. A first weld 518 can extend about a perimeter 520 of the heating element 502, thus surrounding the entire periphery of the heating element 502. A second weld 522 can extend about a perimeter edge 524 of the sheets 504, 506, thus sealing the periphery of the sheets 504, 506 together. In some embodiments, a space 526 between the first weld 518 and the second weld 522 may be totally or partially welded together.

The weld(s) used in some embodiments to create a substantially hermetically sealed shell (e.g., 105; 504, 506) for protecting the heating element (e.g., 310, 502) provides a number of advantages over traditional bonding mechanisms such as sewing, stitches, rivets or grommets that create or reinforce a seal. In certain embodiments of those that employ a heat sealed shell, the external surface of the substantially hermetically sealed shell is not punctured by needle holes, sewing, stitching, rivets, grommets or other fasteners. These traditional fasteners create holes and can accumulate contaminants from blood and body fluids. These holes, crevasses, and fibrous materials such as thread are difficult or even impossible to clean with standard cleaning methods and solutions. Exemplary heating blankets and pads described herein can advantageously have a smooth, non-violated shell, without external attachments or physical places to trap contaminants, thus providing a readily and thoroughly cleanable heating blanket or pad in some embodiments. As will be appreciated, the welded construction used in some embodiments can also facilitate a variety of features that would otherwise require traditional fasteners such as sewing, stitching, riveting, grommets or snaps.

In some embodiments, portions of the shell extending beyond the perimeter of the heating element can form non-heated edge flaps of the heating blanket or pad, such as those described above. Exemplary non-heated edge flaps can preferably extend from 1 inch to 24 inches away from the perimeter of the heating element, although it will be appreciated that any suitable length of extension is possible. The non-heated edge flaps can be used to create a cocoon-like space that traps the heat from the heater in a space around the patient. For example, in alternative embodiments, the edges 112, 114, 116, and 118 of the heating blanket or pad 100 depicted in FIG. 1 can include non-heated edge flaps instead of lateral portions of the heating element 310. The non-heated edge flaps can thus create a thermal barrier between the heater edge and the operating table or bed. In some embodiments, the two sheets of the non-heated edge flaps may be partially or completely welded together between the first weld about the perimeter of the heating element and the second weld about the perimeter of the warming blanket or pad.

Figure 6:
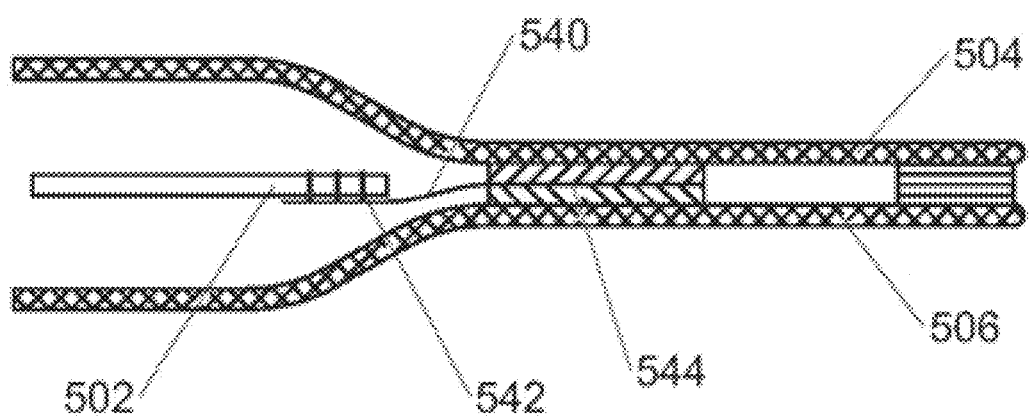
FIG. 6 is a cross-section of a shell containing a heating element secured to the shell according to some embodiments of the present invention.

As previously discussed with reference to at least FIGS. 2A, 4A and 4B, securing strips 317, 371 or securing edges 327 can be provided in some embodiments to facilitate securing the heating element (e.g., 310) to the shell (e.g., 105). With reference to FIG. 6, an exemplary securing strip 540 can comprise a weldable plastic film, for example, a urethane film. A first end 542 of the securing strip 540 can be attached to the heating element 502, for example by sewing. A second end 544 of the securing strip 540 (or securing edge according to alternate embodiments) can be placed between the two sheets 504, 506 and incorporated into the welds between the two sheets. Thus the heater assembly is held in an extended position within the shell, without using stitches, sewing, rivets or grommets that would pierce the flexible material sheets and make the shell difficult to clean.

Embodiments of the heated blanket or pads described herein may be provided as a pad in the form of a heated underbody support. The term underbody support may be considered to encompass any surface situated below and in contact with a user in a generally recumbent position, such as a patient undergoing surgery including heated mattresses, heated mattress overlays and heated pads. Heated mattress overlay embodiments may be identical to heated pad embodiments, with the difference being whether or not they are used on top of a mattress. Furthermore, the difference between heated pad embodiments and heated mattress embodiments may be the amount of support and accommodation they provide, and some pads may be insufficiently supportive to be used alone like a mattress. As such, the various aspects which are described herein apply to mattresses, mattress overlays and pad embodiments, even if only one type of support is shown in the specific example.

Described herein are various embodiments of warming pads that improve patient warming effectiveness by increasing accommodation of the patient into the pad, in other words, by increasing the contact area between the patient's skin and the heated surface of the pad (e.g., heated mattress, mattress overlay). In some embodiments of the pad, as will be further discussed herein, the pad includes not only a heating element, but may also include foam, or could also be air bladders of (e.g., mattress components) that are easily deformable to allow the patient to sink into the pad. This accommodation increases the area of the patient's skin surface in contact with the heated pad and minimizes the pressure applied to the patient at any given point. It also increases the surface contact area for heat transfer and maximizes blood flow to the skin in contact with the heat for optimal heat transfer. Unlike conventional patient warming systems, the accommodation of the patient into the pad is not hindered by a stiff, non-conforming, non-stretching, hammocking heating element. Additionally, in various embodiments, the heating element is at or near the top surface of the underbody support, in thermally conductive contact with the patient's skin, not located beneath thick layers of foam or fibrous insulation.

Various embodiments further provide improved safety. For example, some embodiments provide a heating element that does not produce or reduces "pressure points" against the patient's body, such as against bony prominences, which can occur when a heated pad (or blanket) is stiff.

Figure 7:
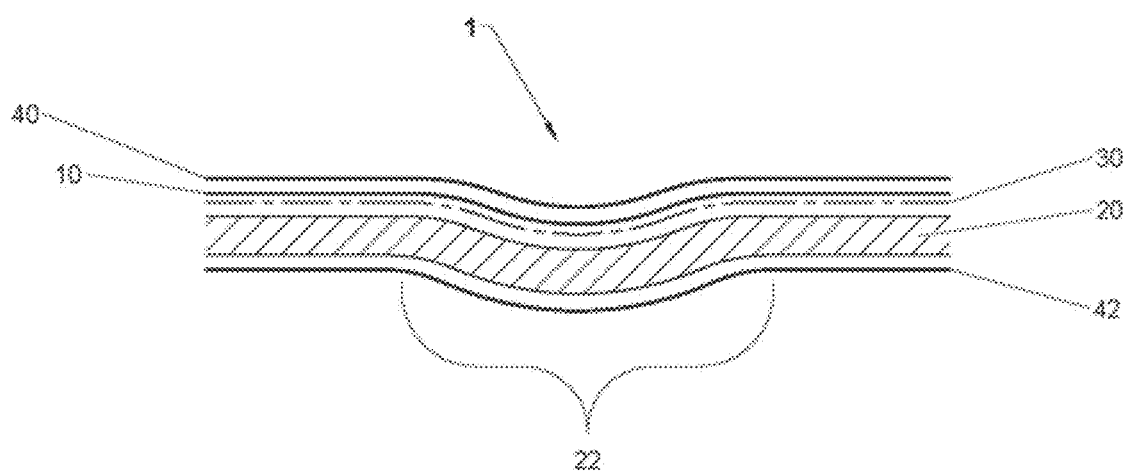
FIG. 7 is a cross sectional view of a heater assembly undergoing deformation in accordance with embodiments of the invention.

FIG. 7 depicts a cross section of a portion of a heater assembly 1. In some embodiments, the heater assembly 1 (e.g., may be same or similar to heating blanket or pad 100, or heating element assembly 350, or any other heaters described herein) including a stretchable fabric heating element 10 (e.g., may be the same or similar to heating elements 310, 502). This example shows the benefits of the stretchable heating element 10, along with a compressible material layer 20 beneath the heating element 10 and bonded to the heating element 10 by a layer of adhesive 30. The heater assembly 1 may include an upper shell 40 and a lower shell 42 (e.g., may be similar to sheets 504, 506). This construction of the heater assembly 1 is favorable because it curves smoothly under pressure from a patient's body (not shown) to stretch into an area of compound curve deformation 22.

In the embodiment shown in FIG. 7 and in several other embodiments, a foam layer 20 is included beneath the heating element 10 (e.g., 310 in FIG. 2A). However, the foam layer 20 may alternatively be described as a layer of compressible material in each of these embodiments and is not limited to foam. For example, the layer of compressible material may comprise gel, stuffing material such as polyester, polyester pellets, bean bag material such as polystyrene beads, air filled compartment, or any material that provides a flexible layer for patient accommodation.

Heat transfer is maximized when the heating element 10 is in conductive thermal contact with the patient. However, as described previously in some embodiments, at least one layer of plastic film is interposed between the heating element 10 and the patient to protect the heating element 10. The one or more layers of thin plastic film may form the upper sheet 40 between the heating element 10 and the patient to introduce minimal thermal resistance to heat flow. In certain embodiments of this invention the fabric heating element 10 may be laminated between two layers of thin (<0.004 in.) and preferably stretchy (e.g. urethane or polyvinyl chloride) plastic films. Laminating a thin layer of plastic film directly onto each side of the heating element 10 protects the heating element 10 fabric from damage by liquids and oxidation. Thin layers of plastic film are sufficient to protect the heating element 10 from liquid and gases, add minimal if any stiffness to the construction, and still allow the heating element 10 to stretch and return to its original shape. This is in contrast to some other conductive fabrics which may require lamination between two thick layers of plastic film in order to provide structural strength and durability, resulting in a stiff and non-stretchable heater.

In some embodiments, the heating element 10 is coated with one or more thin layers of elastomeric materials such as rubber or silicone. The layers of elastomeric material protect the heating element 10 material from damage due to moisture and oxidative chemicals such as hydrogen peroxide. The layers of elastomeric material also provide an electrically insulating layer over the heating element 10 material.

In some embodiments the heating element 10 is also used as a grounding electrode during electro-surgery, the upper layer of elastomeric material forms a second dielectric layer between the patient and the heater, adding to the safety of the device should the outer shell material 40, 42 be cut or pierced. The second dielectric layer prevents a direct electrical contact between the patient and the grounding electrode (e.g., 10).

The pressure relief provided by the pad is maintained by allowing maximal accommodation (allowing the patient to sink into the support) without the heating element assembly creating a "hammocking" force. By allowing maximal accommodation and avoiding hammocking, cutaneous blood flow is maximized at the pressure points, which minimizes the risk of pressure ulcers. The pressure needed to collapse capillaries is said to be 12 to 32 mm Hg. By allowing maximal accommodation and avoiding hammocking, cutaneous blood flow is generally maximized. By maximizing blood flow, the ability of the skin and tissue to absorb heat from the heating element 10 and transfer it to the rest of the body is also maximized. Further, by allowing the patient to sink (accommodation) into the heater assembly 1, the surface area of the heating element 10 in contact with the patient is maximized and thus heat transfer is maximized.

Figure 8:
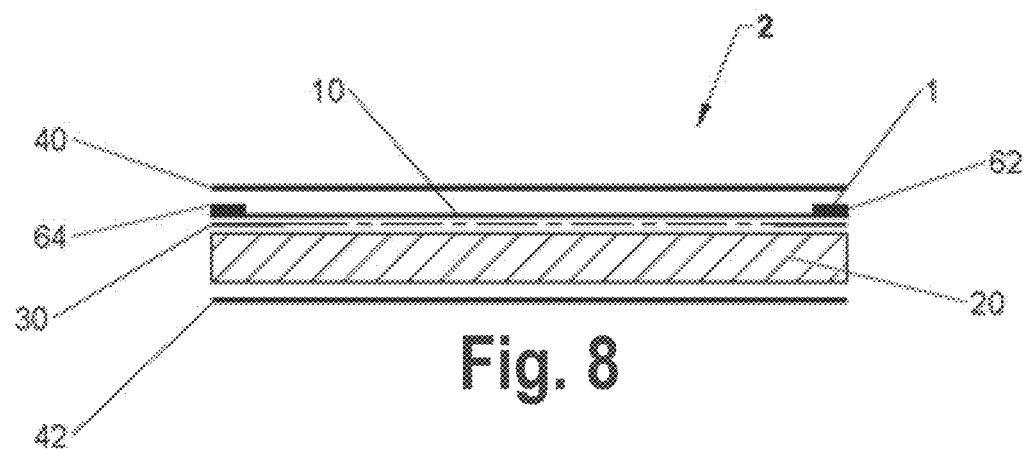
FIGS. 8, 8A and 8B are cross sectional views of a heated mattress overlay or pad in accordance with embodiments of the invention.

When not stretched, fabric heating elements 10 as described herein provide an even heat output or Watt density across their surface, unless they are folded or wrinkled, doubling or tripling the heating element 10 layers in the folded or wrinkled portion. The entire heating element 10 may have a relatively low Watt density, such as less than 0.5 watts per square inch, for example. Therefore, it is preferable to prevent local wrinkling of the heating element 10. An embodiment of a heated pad 2 in the form of a heated underbody support, a heated mattress, or a heated mattress overlay includes a heater assembly 1 and a compressible material layer (e.g., foam layer) 20 and having reduced wrinkling or folding is shown in FIG. 8. It should be noted, however, that whether a unit is described as a heated mattress, heated mattress overlay or heated pad is largely unimportant, and most embodiments could be used variously as heated underbody supports. While a heated mattress overlay or blanket may have no layer of padding or may have a thinner layer of padding, a heated pad typically has padding that may be thin or thick, a heated mattress may have an even thicker layer of padding. As such, various embodiments of the pad may be used alone, in the manner of a mattress, or on top of a mattress, in the manner of a mattress overlay. Descriptions relating to heated mattress overlays therefore also apply to descriptions of heated mattresses and heated pads, and vice versa.

The compressible material layer 20 (e.g., FIG. 8) may be a single layer or may be a stack of materials that includes a layer of foam. This stack could include foam layers of different densities, different accommodation properties, different stiffness or different polymers. Additionally, the stack of materials can include other materials such as woven or non-woven fabrics or films, to achieve other characteristics such as lateral stiffness or durability and strength. The term compressible material layer 20 therefore refers generally to single layers of foam as well as multilayered stacks that include one or more layers of foam and may include other materials. Also, the layer of foam may alternatively be a layer of compressible material as described above.

As shown in FIG. 8, the attachment of the heating element 10 to the compressible material layer 20 may be achieved by adhesive bonding 30 across the entire interface between the two. The bond may be made with an adhesive comprising a pressure-sensitive adhesive without a reinforcing fiber or film carrier. Since the compressible material layer 20 is preferably flexible, stretchable and compressible, such a bonding made with such an adhesive does not alter the flexibility and stretch-ability of the heating element 10 or heated mattress overlay or pad 2. Alternately, the heating element 10 may be attached to the compressible material layer 20 only along one or more of the edges 12, 14, 16, 18 (16 and 18 not shown in FIG. 13, but similar and generally perpendicular to edges 12 and 14). In some embodiments the heating element 10 may be attached to the compressible material layer 20 only along one or more edges such as along two opposing edges such as edges 12, 14, or in an intermittent pattern.

Figure 10:
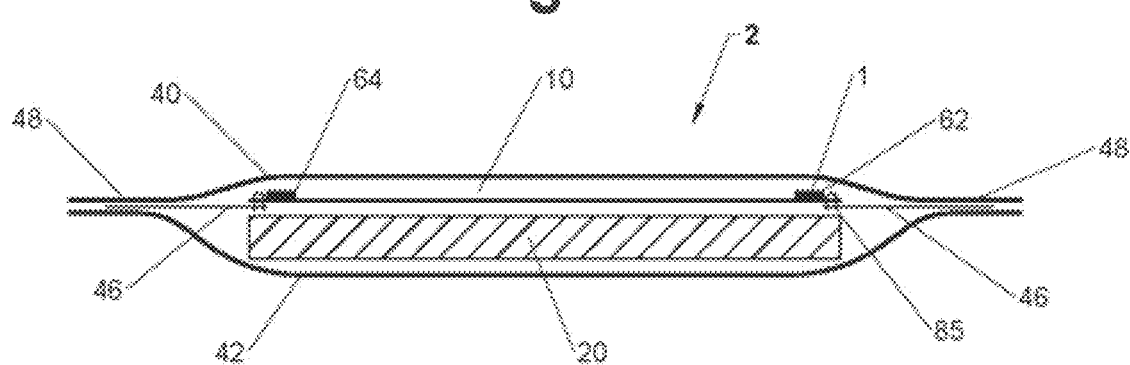
FIG. 10 is a cross sectional view of a heated mattress overlay or pad in accordance with embodiments of the invention.

An alternative embodiment is shown in the heated pad 2 which is shown in FIG. 10. In this embodiment, the fabric heating element 10 is anchored to the shell including the upper shell 40 and the lower shell 42 along its edges and thus held in an extended and wrinkle-free condition. Anchoring strips 46 comprised of plastic film or a suitable alternative are attached along the edges of the heating element 10, preferably by sewing to form a sewn connection 85, though other forms of attachment may be used such as adhesive bonding. The anchoring strips 46 extend along all four edges of the heating element 10 to form a peripheral bond 48. Alternatively, the anchoring strips 46 may extend along only one pair of opposing edges such as edges. The anchoring strips 46 may be made of the same material as the shells 40, 42, such as plastic film, and therefore can be bonded around the periphery of the heated pad 2, being sandwiched between and incorporated into the bond between the upper shell 40 and the lower shell 42.

Figure 9:
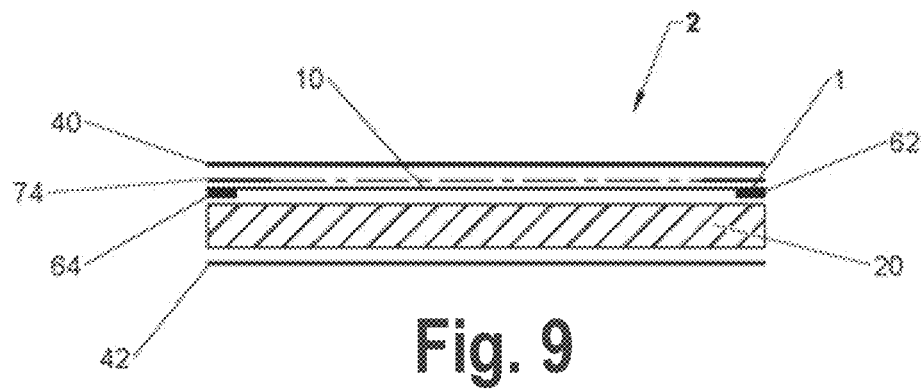
FIG. 9 is a cross sectional view of a heated mattress overlay or pad in accordance with embodiments of the invention.

Some embodiments maintain the heating element 10 in an extended and unwrinkled condition. It may be preferable in order to avoid hot spots, that more than one heating element 10 anchoring embodiment be used simultaneously. To maintain flexibility, conformability and stretchability, the upper and/or lower shell 40, 42 may be adhered to the heating element 10 or the compressible material layer 20, across their broad surfaces as shown, for example, in FIG. 9, or may not be so adhered. However, in some embodiment the heating element 10 can be bonded to the upper shell 40, for example. This may be advantageous for minimizing wrinkling of the heating element 10 or plastic film layer of the shell 40, 42.

The compressible material layer 20 (or layer of compressible material) supporting the heater assembly 1 in certain embodiments of this invention could be almost any thickness that is advantageous for the given application (for example, 0.5-6.0 inches). The compressible material layer 20 may be uniform in thickness and density or it may be contoured in thickness, shaped, scored or segmented according to areas of different densities.

As shown in FIGS. 11-13, the portions of the heating element 10 attached to bus bars 62, 64, which may include any of the features described with respect to bus bars 315. In the exemplary embodiment of FIGS. 11-13, bus bars 62, 64 are preferably bonded to the compressible material layer 20 along beveled ends 22, 24. Locating the bus bars 62, 64 on the beveled ends 22, 24 of the foam layer 20 provides some protection of the bus bars 62, 64 from mechanical stress when patients are sitting or lying on the heated pad 2. Alternatively, to provide additional protection to the bus bars 62, 64, the heating element 10 may be wrapped around the compressible material layer 20 and onto a bottom surface 23 so that the bus bars 62, 64 are located under the foam layer beveled ends 22, 24 and attached to the bottom surface 23 as shown in the cross section shown in FIG. 12, for example. In a further alternative shown in FIG. 13, the beveled piece of compressible material that is removed from the compressible material layer 20 or any other triangular or wedge shaped piece of compressible material of complementary size and shape to fit the space may be bonded over the heater assembly's bus bars 62, 64, along the beveled edges 22, 24 of the compressible material layer 20 to form a filler 25, to fill in the beveled space and protect the bus bars 62, 64. The compressible material filler 25 may be sized such that, when in place above the bus bars 62, 64, the horizontal upper surface of the heated pad 2 above the central, non-beveled portion of the compressible material layer 20, is level with the horizontal upper surface of the overlay 2 above the beveled end 24. In these embodiments the heating element 10 extends across an upper surface 21 of the compressible material layer 20, and the bus bars 62, 64 are away from and lower than the upper surface 21. In this way, the bus bars 62, 64 may be physically protected from damage by bonding them onto or beneath the beveled edges 22, 24 of the compressible material layer 20, where they are effectively recessed from the upper surface 21 of the foam layer 20. The beveled edges 22, 24 of the compressible material layer 20 allow the bus bars 62, 64 to be optionally covered with a compressible material filler 25 to act as a protective barrier in this location for added protection, without adversely affecting the look of the smooth top surface of the heated pad 2, thereby basically filling the bevel space with a compressible material filler 25 to create an overall rectangular cross sectional shape.

In some embodiments, the combination of conductive fabric heating elements 10 made from flexible and stretchable material, bus bars 62, 64 attached near opposing edges 12, 14 of the heating element 10, one or more temperature sensors and a controller, comprises a heater assembly 1 according to some embodiments. The heater assembly 1 may be secured to a compressible material layer 20 such as foam and may be covered with a water-resistant shell 40, 42 that is preferably made of a stretchable plastic film such as urethane or PVC, however, other film materials and fiber-reinforced films are anticipated.

Figure 19:
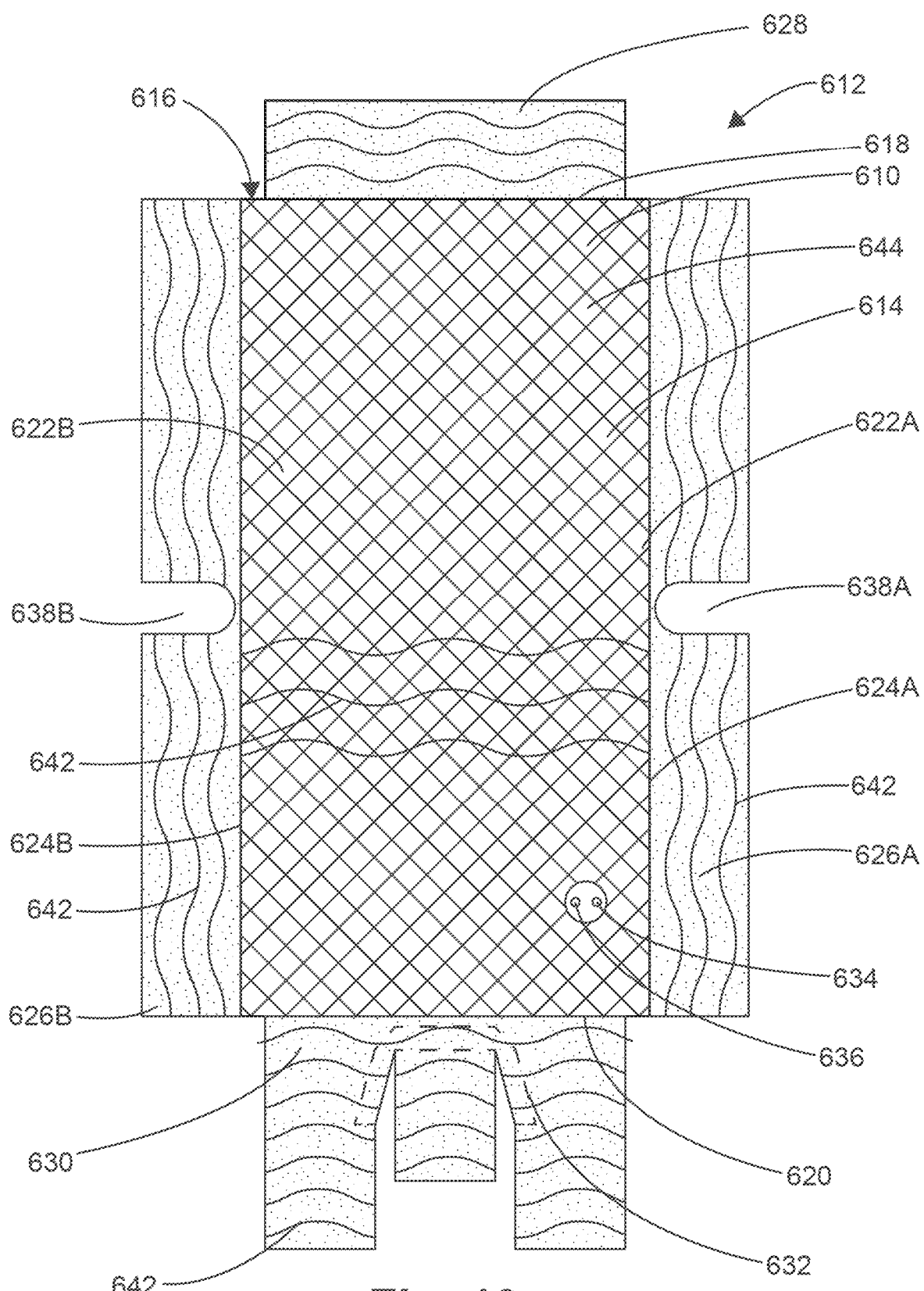
FIG. 19 is a top plan view of a heating element assembly, which may be incorporated in a heated mattress, such as that shown in FIG. 18.

In some embodiments, a portion of the compressible material layer 20 is thinned or scored in an area, from one lateral edge to the other of the area, with the area located to overlie the location of transition from one cushion of an operating table to the adjacent cushion under normal conditions of use. Preferably the thinning or scoring is on the bottom surface 23 of the compressible material layer 20 and therefore away from the patient contact top surface 21. Since operating room tables are designed to flex at this location between the operating table cushions, a thinned compressible material layer 20 at the location of transition between cushions will aid in flexion of the heating element 10 and reduce the chances of the heating element 10 wrinkling during flexion. Alternatively, the compressible material layer 20 could be scored or cut or otherwise have one or more gaps or channels completely through or partially through its thickness on the bottom surface 23 at the flexion locations or other areas where added flexibility may be desirable, as shown in FIG. 19, for example. In the embodiment shown, multiple small channels 27 are present in a portion of the compressible material layer 20 where the compressible material layer 20 is thinner. These channels 27 may extend across the compressible material layer 20, from one end to the opposing end, such as across the width or the length of the compressible material layer 20, such as in a direction parallel to and aligned with the transition between operating table cushions. In use, the pad 2 may be positioned over a table or bed with which it is designed to be used such that the channels are located over the flexion locations of the table or bed. The table or bed may then be adjusted by bending at a flexion point (such as to raise or lower a patient's upper body or legs by bending or extending the patient at his or her hips) and the compressible material layer 20 of the heated pad 2 can bend easily at this location due to thinness or scoring at the location of flexion, while the heating element 10 can likewise bend without wrinkling or folding due to its flexibility and elasticity.

In some embodiments, and as shown in FIG. 14, the compressible material layer 20 may be thinned or scored or have gaps or channels 27 longitudinally in order to increase flexibility for bending the heated pad 2 around a longitudinal axis such as a long axis of a body. This may be advantageous to aid in wrapping the heated pad 2 around a patient being positioned within a "bean bag" or "peg board" positioner. The longitudinal thinning or scoring or presence of gaps or channels 27 allows the heated pad 2 to be wrapped around the dependent portion of the patient, increasing the area of surface contact between the heating element 10 and the skin while avoiding wrinkling of the heating element 10 due to the bending of the compressible material layer 20.

In addition to the warming features described herein, in some embodiments and as shown in FIG. 8, the heating element 10, which is already in close proximity to the underside of the patient, is a capacitive coupling grounding electrode 10. By using the heating element material 10 as the grounding electrode 10, there is no competition to determine which technology is going to be in the most advantageous position—close to the patient's skin. Both technologies get the same advantageous location. Using a single piece of conductive material, preferably a stretchable conductive or semi-conductive fabric as the heating element 10 and grounding electrode 10, also minimizes the negative effects of multiple layers of materials and laminates being interposed under the patient, which can cause hammocking, thereby reducing the pressure off-loading abilities of the mattress. The fewer the layers of material, the more stretchable and flexible the construction. Avoiding constructions that involve layers of fabric and film to be bonded together forming laminates is performed in order to optimize stretchability and flexibility.

A semi-conductive polymer such as polypyrrole is advantageous in that it is a preferential RF energy absorber. Polypyrrole can also be polymerized onto fabric and in the process coats each individual fiber, retaining the flexibility and stretchability of that fabric. The polymerization process results in a bond between the fiber and the polymer that is inseparable. This is in contrast to electrically conductive composites made from powdered or vaporized carbon or metals that may be applied to the surface of relatively non-stretching fibers and fabrics such as woven nylon, because such composites will flake off with repeated flexion and stretching. Polypyrrole is, therefore, a preferable conductive material for heaters and grounding electrodes that are to be positioned under a patient because it allows flexion and stretching so that the patient can sink optimally into the support surface below the heating element and/or grounding electrode (e.g., 10).

Figure 8A:
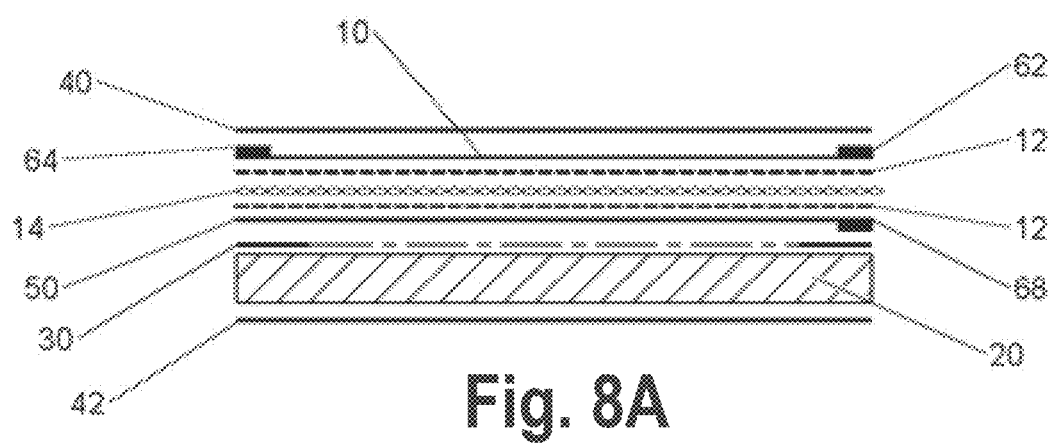

As shown in FIG. 8A, in some embodiments the grounding electrode 50 is a separate layer of material positioned near and parallel to the heater 10. In this case, the grounding electrode 50 may advantageously be made of a semi-conductive polymer such as polypyrrole irrespective of what the material the heating element 10 is made. The heating element 10 and grounding electrode 50 may be electrically insulated from each other by applying a coating of elastomeric material 12 such as silicone or rubber to one or both conductors. A layer of electrically insulating material 14 such as fabric, film or foam may be interposed between the heating element 10 and grounding electrode 50. Preferably these layers of electrically insulating materials are not all bonded together into a laminate that would add unnecessary stiffness to the support surface.

Figure 8B:
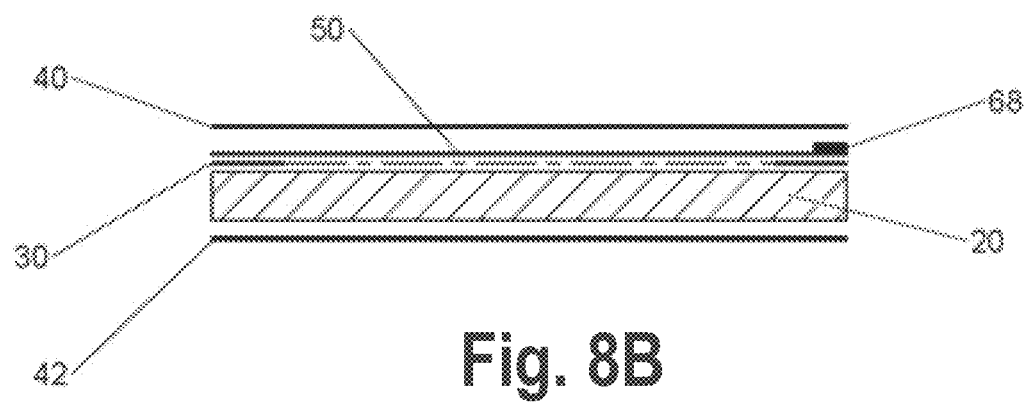

As shown in FIG. 8B, in some embodiments, the grounding electrode 50 is its own layer of material, and there is no heater (e.g., heating element 10). In these cases, the grounding electrode may advantageously be made of a semi-conductive polymer such as polypyrrole because of its flexibility, stretchability, durability, radiolucency and radar-absorbing attributes, compared to other metal coated fabrics.

In certain embodiments of the invention as in FIGS. 8A and 8B, the grounding electrode 50 is electrically connected via an electrical conductor, or bus bar 68. The bus bar 68 of some embodiments of this invention may be attached to the grounding electrode 50 by sewing with electrically conductive thread. This construction maintains flexibility and durability with repeated flexing. The sewn connection between the bus bar 68 and the grounding electrode 68 according to embodiments of the invention results in a connection that is very robust, flexible and tolerant of extreme flexing and resistant to degradation.

According to some embodiments, the bus bar 68 is coupled to the grounding electrode 68 by a stitched coupling, for example, formed with electrically conductive thread such as silver-coated polyester or nylon thread (Marktek Inc., Chesterfield, MO), extending through the grounding electrode (e.g., 10 or 50) and through the bus bar 68. Alternative threads or yarns employed by embodiments of the present invention may be made of other polymeric or natural fibers coated with other electrically conductive materials. In addition, nickel, gold, platinum and various conductive polymers can be used to make conductive threads. Metal threads such as stainless steel, copper or nickel could also be used for this application. According to an exemplary embodiment, the bus bar 68 may be comprised of flattened tubes of braided wires; for example, a flat braided silver coated copper wire, and may thus accommodate the attaching thread extending there through, passing through openings between the braided wires thereof. In addition, such bus bars 68 are flexible, thereby enhancing the flexibility of the mattress heater assembly. According to alternate embodiments, the bus bar 68 may be a conductive foil or wire, flattened braided wires not formed in tubes, an embroidery of conductive thread, a printing of conductive ink, or other suitable bus bar construction.

In some embodiments, the dielectric is the outer shell material 40 of the underbody support (mattress overlay or pad 2). In some embodiments, other layers of material such as fabric or foam 74 (FIG. 9) may be interposed between the shell dielectric material 40 and the heater/grounding electrode material 10. In some embodiments, these layers of materials are preferably not laminated together, thereby maintaining maximal flexibility and stretchability for accommodating the patient into the pad 2.

In some embodiments, one or both sides of the grounding electrode layer 10, 50 (and/or heating element 10) is coated on its upper side with a thin layer of flexible, stretchable elastomeric material such as rubber or silicone. This coating of elastomeric material interposed between the electrode and the dielectric material layers serves as second, redundant, safety dielectric layer should an inadvertent hole be put into the outer shell. The redundant dielectric layer would prevent direct electrical coupling between the patient and the grounding electrode material 10, 50, which could cause a burn.

Preferably, the elastomeric material is applied as a gel or liquid so that it can coat the individual fibers of the heating element material (e.g. 310, 502, 10) before it sets up into its elastomeric solid form. Coating the individual fibers maximally protects the heating element, from moisture damage. It also limits the electrical contact area to an inadvertently cut edge in the exceedingly unlikely event that the both the dielectric and heater layers are cut and the active electrode of the electrosurgical unit is inserted into the cut. In this instance the polymeric heaters fibers at the cut edge would melt and retract from the electrode, automatically limiting the adverse current flow.

In some embodiments, the return electrode wire 70 is electrically connected 72 directly to the grounding electrode material 10. Since the grounding electrode 10 is the heating element 10, the electrode itself adds resistance to the current flow through the circuit. The further the current may flow through the heater material, the greater the resistance. A return electrode wire 70 connected 72 to one end of the heating element 10 would create a situation wherein the electrical resistance to current flow would be significantly greater for current originating at the far end compared to the end of the patient closest to the wire connection 72.

In some embodiments, the return electrode wire 70 is electrically connected 72 to one of the bus bars 62, 64. Connecting the return electrode wire 70 to the bus bar 62 or 64 is advantageous when the grounding electrode material is a resistive heating element 10 that adds resistance to the circuit. Since the low resistance bus bar 62, 64 runs substantially parallel to the patient along an edge of the grounding electrode, the resistance to the current flow caused by the heater material is substantially equal along the entire length of the patient that is contacting the grounding electrode creating a safe condition.

In some embodiments, the shared conductive pathway through the heating element 10 involves that the capacitive coupling electrode of the instant invention be adapted to hook to patient warming power supplies and electrosurgical generator that are designed with a "floating" output. By "floating," we mean that the electrical current within each of the respective circuits has no potential or reference with respect to earth (ground) or with respect to the other piece of equipment. This configuration allows simultaneous operation of the patient warming power supply and electrosurgical generator without electrical interference occurring between the two.

In some embodiments, the shared conductive pathway through the heating element 10 may require that the capacitive coupling electrode of the instant invention be adapted to hook only to patient warming power supplies that supply a low voltage direct current (48 volts or less) and an electrosurgical unit that supplies an RF current. This configuration helps to allow simultaneous operation of the patient warming power supply and electrosurgical unit without electrical interference occurring between the two.

In FIGS. 7 and 11, the shell 40, 42 protects and isolates the heater assembly 1 from an external environment of the heater assembly 1 and may further protect a patient disposed on the heated pad 2 from electrical shock hazards. According to preferred embodiments, the shell 40, 42 is waterproof to prevent fluids, for example, bodily fluids, IV fluids, or cleaning fluids, from contacting the heater assembly 1, and may further include an anti-microbial element, such as SILVERion® antimicrobial fabric available from Domestic Fabrics Corporation (Kinston, North Carolina), which is extruded in the plastic film of the shell material.

As shown in FIGS. 10 and 11, in some embodiments, a layer of plastic film is placed over each broad surface of the heater assembly 1, as an upper shell 40 and a lower shell 42 but is not bonded to the heater assembly 1. The two layers of plastic film are bonded to each other around a periphery 48 of the heater assembly 1 to form a water-resistant shell. The bond may be from heat, radio frequency (RF), ultrasound, solvent or adhesive, for example. The heater assembly 1 may be "free floating" within the shell with no attachment to the shell, or can be attached to the shell, such as only at the edges of the heater assembly 1 as described above, for example. This bond construction around the periphery 48 of the heated pad 2 creates a durable shell without folds, creases, crevasses or sewing needle holes that can collect infectious debris and be difficult to clean. The heater assembly 1 covered by a shell of plastic film and optionally including a foam or other support layer comprises a heated mattress, mattress overlay, or pad according to some embodiments.

Figure 15:
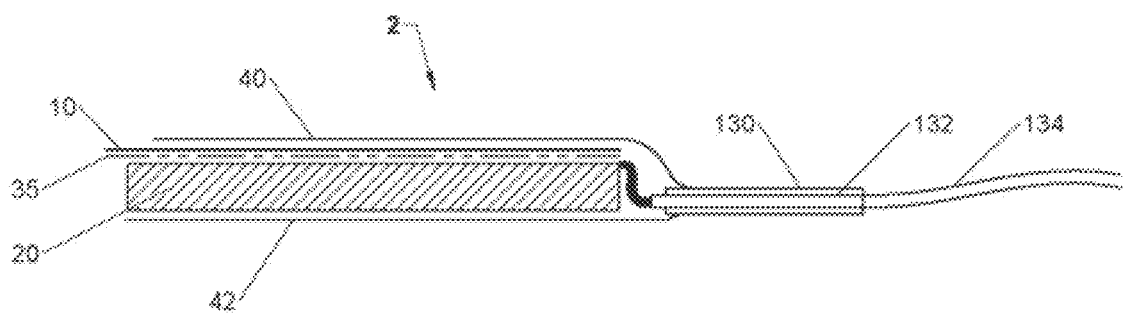
FIG. 15 is a cross sectional view of a heated mattress overlay or pad with a power entry assembly located in the peripheral bond between the shell layers in accordance with embodiments of the invention.

FIG. 15 depicts a cross section of a portion of an alternative embodiment of a heated pad 2, in which the fabric heating element 10 is bonded to an overlaying plastic film layer comprising an upper shell 40 by a layer of adhesive 35. In such embodiments, the upper shell 40 can be stretched and held in position by the compressible material layer 20 or by anchoring the heated pad 2 laterally, with or without bonding the shell 40, 42 to the heating element. When the stretched layer of upper shell material 40 is bonded to the heating element 10, this may reduce or prevent wrinkling or folding of the heater element 10 and yet maintain flexibility and stretchability (depending on the stretchability of the shell material). In the embodiment shown, the heated pad 2 further includes a lower shell 42 beneath the compressible material layer 20.

Figure 16:
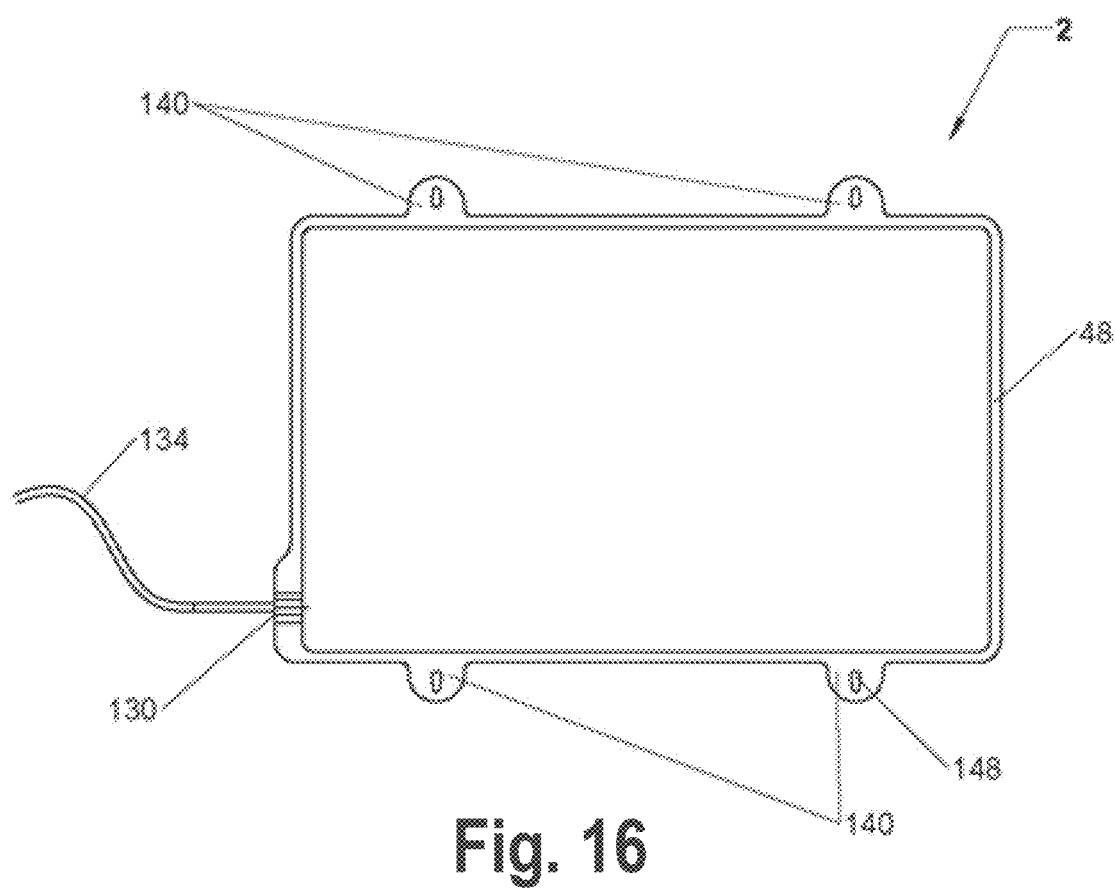
FIG. 16 is an illustration of a heated mattress overlay or pad with attachment tabs in accordance with embodiments of the invention.

In certain embodiments, such as the embodiments shown in FIGS. 15 and 16, the shell construction allows a power entry module 130 to be located and bonded between the shell, such as the layers of plastic film 40, 42, at the edge of the shell within the bonded layers 48. The power entry module 130 can be bonded with adhesive, solvent or heat, for example, between the adjacent layers of upper and lower shell 40, 42. Sewn shell constructions known in the art prevent the power entry from being located at the sewn edge and result in the power entry being located on the flat surface of the shell rather than the edge, which may result in the patient laying on the hard lump created by the power entry module and which could contribute to the formation of a pressure injury. In some embodiments, the power entry module 130 is a piece of molded plastic, for example in a shield-shape, that can be sealed between the sheets 40 and 42 in the peripheral bond 48 edge seal of the shells 40, 42. The pointed ends of the shield-shaped power entry module 130 allows the shells 40, 42 to transition smoothly from the area where the upper and lower shells 40, 42 are sealed to each other, to the adjacent area where the shells 40, 42 are sealed to the power entry module 130 and then back to the shells 40, 42 being sealed to each other. In some embodiments, the power entry module 130 includes a tubular channel 132 traversing from the outer side to the inner side of the shell. The tubular channel 132 may be sized to accommodate a wire cable 134 that contains the power and sensor wires. The wire cable 134 can pass through the tubular channel 132 from the outside to the inside of the heated pad 2 and can be adhesive, solvent or heat bonded to the power entry module in this position, creating a water-tight seal. In another embodiment, the power entry module 130 may be shaped and sized to house a plug-in connector. In some embodiments, the return electrode wire 70 that connects to the electrosurgical generator can pass through an identical tubular channel 132 from the inside to the outside of the heated pad 2 as the power entry module 130, which is used for the power cable 134 to exit the shell.

The heated underbody support may have two or more attachment points such as tabs 140 for securing the support over the top of a surgical mattress or table such as is shown in FIG. 15. These attachment points may be tabs 140 or flaps made from shell material that extend outward from the peripheral bond 48 of the shell. These attachment points may be fiber-reinforced and yet flexible and somewhat loose, so that they do not cause hammocking of the shell. The attachment points can be secured to the table with many different means including straps, ties, loops, hooks, snaps, barbs, Velcro or other attachment means.

The heater assembly 1 of these inventions can be encased in a shell of plastic film as described, or may have no shell. With or without a shell or compressible material layer 20, it can be used alone, or it can be used as a mattress overlay on top of, or can be inserted into, a pressure reducing mattress. For example, since pressure reducing mattresses typically have water resistant covers, the heater assembly 1 may be inserted directly into the mattress, inside the mattress cover, without a shell on the heater assembly 1. In either case, the heater assembly 1, or heated pad 2 is designed to have little or no negative impact on the pressure reducing capabilities of the mattress on which it is laying or into which it is inserted.

The heated pad 2 may have two or more attachment points such as tabs 140 for securing the support over the top of a surgical mattress or table such as is shown in FIG. 24. These attachment points may be tabs 140 or flaps made from shell material that extend outward from the peripheral bond 48 of the shell. These attachment points may be fiber-reinforced and yet flexible and somewhat loose, so that they do not cause hammocking of the shell. The attachment points can be secured to the table with many different means including straps, ties, loops, hooks, snaps, barbs, Velcro or other attachment means.

The shell of the heater assembly 1 is preferably water resistant, flexible, and durable enough to withstand the wear and tear of operating room use. Examples of materials which may be used for the shell include urethane and PVC. Many other suitable plastic film or fiber-reinforced plastic film shell materials are anticipated. In some embodiments, the shell material is about 0.010-0.015 inch thick. In this thickness range, both urethane and PVC, for example, are strong but retain an adequate stretchability. The heated pad 2 may cover approximately the entire surface of the surgical table or any other bed. Alternately, the heated pad 2 may be sized to fit some or all of the cushion that form the support surface of a surgical table. For example, if the cushion has multiple separate sections, such as three, the heated pad 2 may be sized to fit over one or two or all three of the cushion sections.

Figure 17:
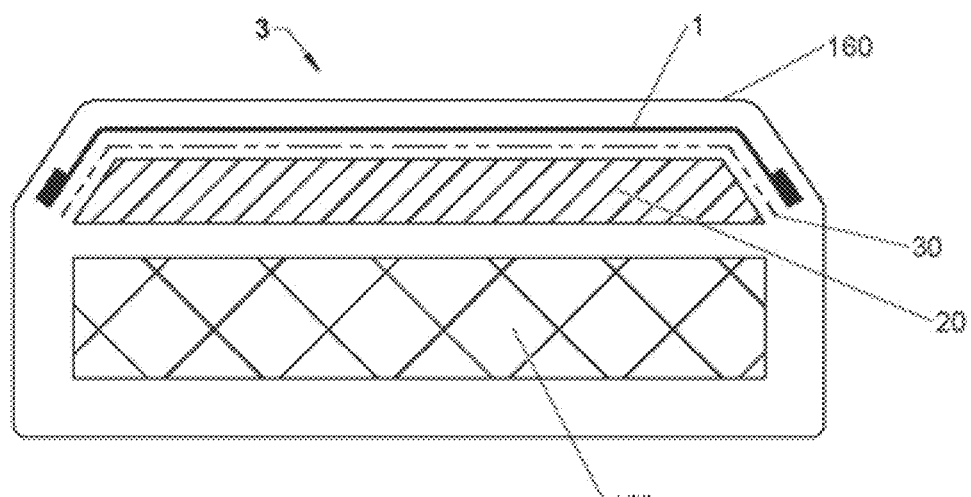
FIG. 17 is a cross sectional view of a heated mattress including a visco-elastic foam layer in accordance with embodiments of the invention.

As shown in FIG. 17, in some embodiments, compressible material layer 20 or a foam layer 150 may be high tech foam to reduce the pressure exerted against the patient's skin during surgery. High tech foams include but are not limited to visco-elastic foams that are designed to maximize accommodation of the patient into the mattress (e.g., pad). As previously noted, accommodation refers to the sinking of the user, such as the patient, into the pad 2 until a maximal amount of support surface area is in contact with a maximal amount of skin surface, and the pressure exerted across the skin surface is as uniform as possible. These high tech foam materials may accommodate the patient more effectively than simple urethane upholstery foam. Unlike other mattress heaters or heating materials, the unique stretchable, flexible, free floating design of the heater assemblies 1 described herein allow them to overlay a layer of visco-elastic foam and maintain the accommodation properties of the foam. Further, the heater assembly 1 of this invention is soft, flexible and stretchable enough to be the separated from the patient by only a single layer of plastic film and still be comfortable. The avoidance of multiple layers of materials interposed between the patient and the mattress foam maximizes accommodation and heat transfer.

In embodiments comprising heated mattresses 3 including foam layers 150, a water-resistant shell or cover 160 may encase the foam 150 as shown, for example, in FIG. 17. The foam 150 may be simple urethane foam or high-tech foam such as visco-elastic foam, for example. The cover 160 may be made of plastic film that has been extruded onto a woven fabric (e.g., Naugahyde), for example. In one embodiment, the heater assembly 1 may be located within or may be removably inserted directly into the mattress cover 160, with or without a shell 40 on the heater assembly 1. The heater assembly 1 may be placed directly on top of the mattress foam 150 inside the cover 160 or a heater assembly 1 (with its own shell) may be placed on top of a mattress outside of the mattress cover 160. If a foam mattress has its own shell, the thickness of the shell 40 of the heater assembly 1 can be reduced to, for example, about 0.003 and about 0.010 inch, or even omitted, because the heater assembly 1 is protected from mechanical damage by the cover 160 of the mattress 150. The thinner shell material improves the stretch-ability of the shell. Alternately, the heating element 10 may be bonded directly to the mattress foam 150.

The thermal effectiveness of this heated underbody support can be optimized when the heating element 10 is overlaying a layer that can provide maximal accommodation of the patient positioned on the support. In this condition, the heating element 10 is in contact with a maximal amount of the patient's skin surface which maximizes heat transfer. Heated pads made with inflatable air chambers forming or included in the compressible material layer 20 or in addition to the compressible material layer 20, can provide excellent accommodation. Further, a heated underbody support with excellent accommodation properties having a heating element 10 as described herein avoids degrading the accommodation properties of the mattress when a heater assembly 1 is added.

In some examples, as shown in FIGS. 18-21, the heating pad may be in the form of a heated mattress 602. The heated mattress 602 can include a heater assembly 612 that includes a flexible sheet-like heating element 610. In some examples, the flexible sheet-like heating element 610 is made of a semi-conductive polymer, such as Polypyrrole, that has been polymerized onto a non-conductive woven or non-woven fabric, such as polyester. Other flexible heating element materials and constructions can be used, including those have been previously disclosed herein. In some examples, electrically conductive bus bars 624A, 624B are attached at or near side edges 622A, 622B of the flexible sheet-like heating element 610. Bus bars and bus bar attachments, have been previously disclosed herein, and, in some cases, the bus bars 624A, 624B, located at or near side edges 622A, 622B of heating element 610, can include any or more features previously described and/or illustrated herein. In some examples, such as that illustrated, fabric side edge extensions 626A, 626B, a fabric upper edge extension 628 and a fabric lower edge extension 630 may be attached by sewing, adhesive, or other attachment means to the respective side edges 622A, 622B, upper edge 618 and lower edge 620 of the heating element 610.

Figure 18:
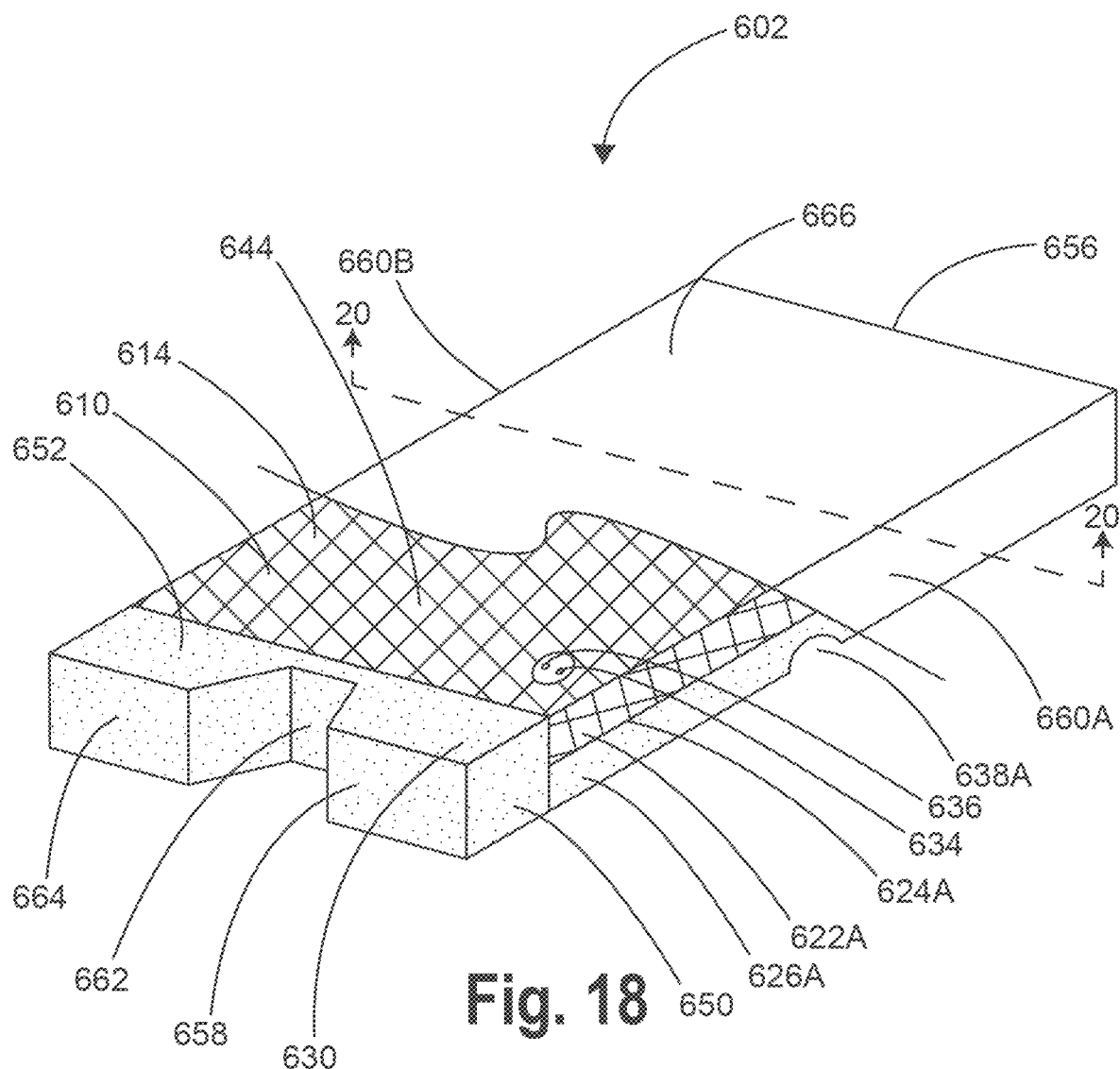
FIG. 18 is a partial cutaway perspective view of a heated mattress in accordance with embodiments of the invention.
Figure 20:
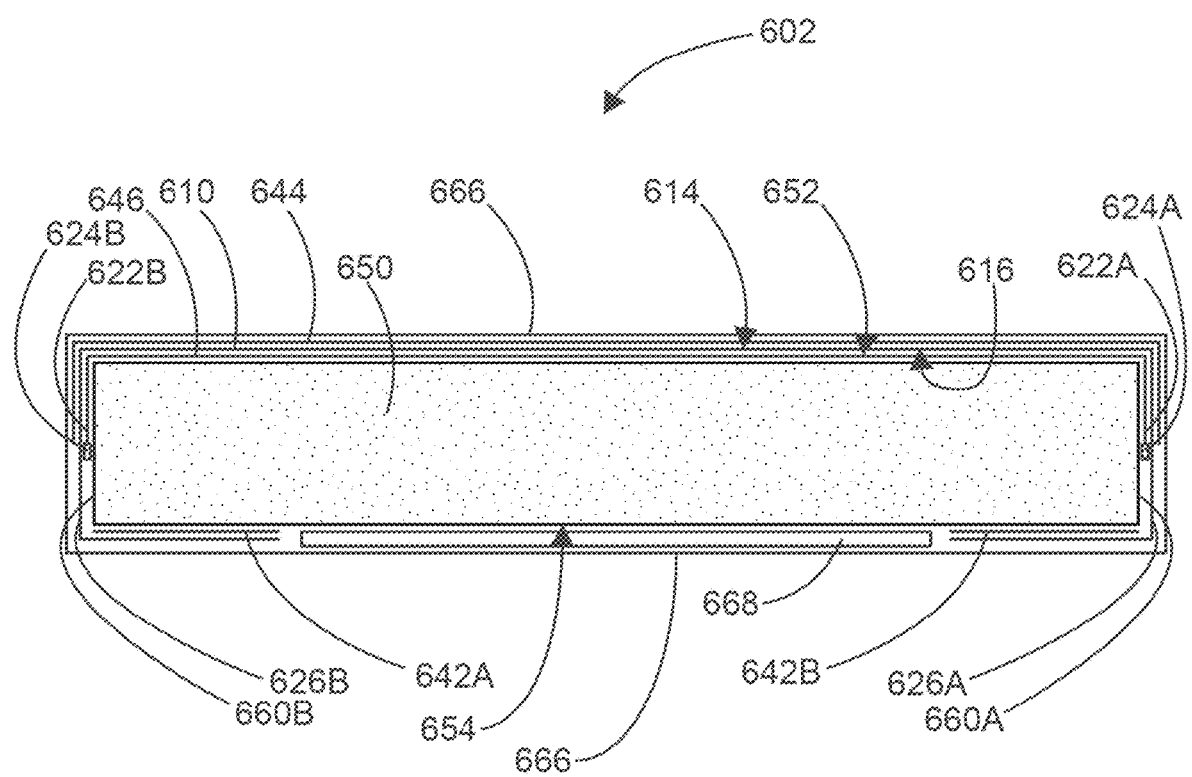
FIG. 20 is a cross sectional view of a heated mattress, such as that shown in FIG. 18, in accordance with embodiments of the invention.
Figure 21:
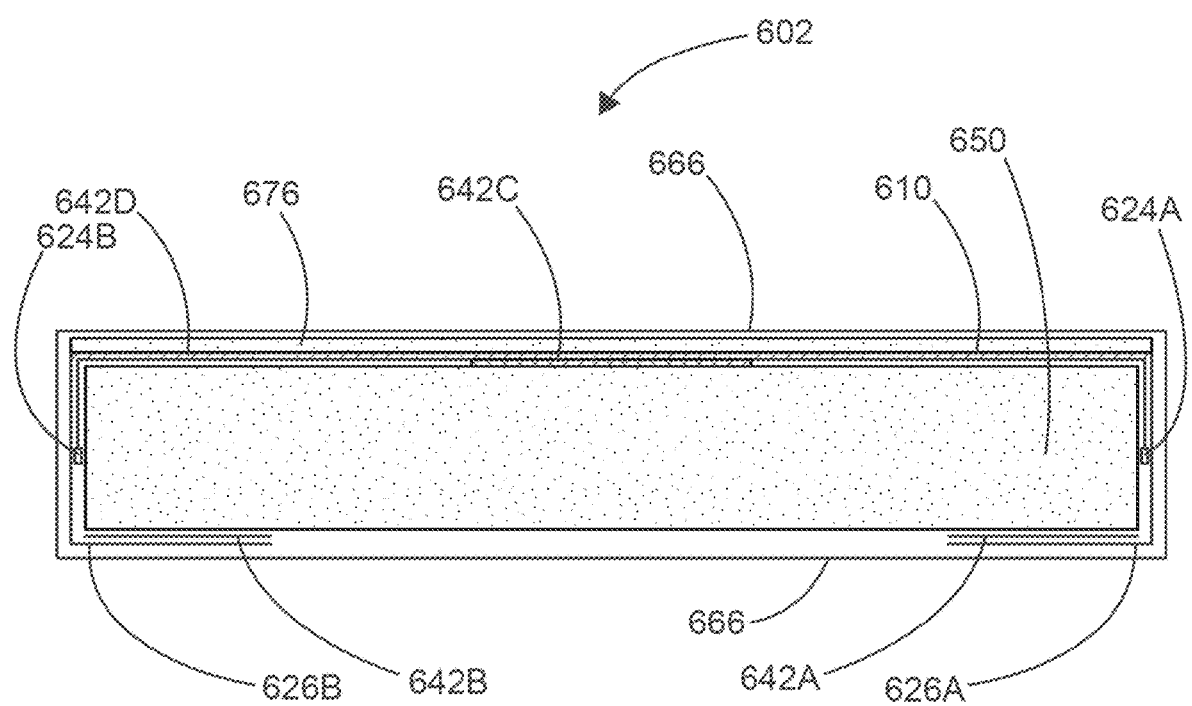
FIG. 21 is a cross sectional view of a heated mattress, such as that shown in FIG. 18, in accordance with embodiments of the invention.

In some examples, as shown in FIGS. 18, 20 and 21, the heated mattress 602 can include a polymeric foam compressible material layer 650. In some examples, the foam layer 650 includes a top surface 652, a bottom surface 654, an upper wall 656, a lower wall 658 and two side walls 660A, 660B. In some examples, the foam layer 650 is made of urethane foam or elastomeric memory foam, though other foam materials can be utilized. In some examples, the foam layer 650 can include two or more layers of different foam materials (e.g., attached together, such as adhesively laminated together) to enhance various qualities of the foam layer 650. In some examples, the upper most layer of foam may be a softer, lower density urethane foam or a softer, lower density elastomeric memory foam and the bottom layer(s) of foam may be a denser urethane foam that prevents "bottoming out." In some examples, the heated mattress 602 may include a polymeric foam compressible material layer 650 that has been hollowed out to substantially form a foam box in which transverse inflatable air tubes can be housed, creating a combination foam and air mattress.

In some examples, the heating element 610 may be sized to extend across a width equal to a width of the top surface 652 of the foam or air, compressible material layer 650 (e.g., extend across an entire width of the top surface 652) and extend at least part way down a direction of the side walls 660A, 660B of the compressible material layer 650. In some examples, the electrical bus bars 624A, 624B are attached near the side edges 622A, 622B of the heating element 610 (e.g., the electrical bus bars 624A, 624B are attached at the portion of the heating element 610 that extends at least part way down the direction of the side walls 660A, 660B and near the side edges 622A, 622B of the heating element 610). When the heating element 610 wraps over the side edges of the top surface 652 of the compressible material layer 650, the bus bars 624A, 624B are advantageously located adjacent the side walls 660A, 660B of the foam layer 650. In this bus bar position, the bus bars 624A, 624B can be protected from flexing each time a patient sits on the mattress 602, in contrast to locating the bus bars 624A, 624B at a location on the top surface 652 of the foam layer 650.

In some examples, the heating element 610 and bus bars 624A, 624B are substantially unattached to the side walls 660A, 660B of the foam compressible material layer 650 (e.g., and spaced apart from the side walls 660A, 660B), to allow for substantially free movement and prevent sharp flexing. In some examples, the bus bars 624A, 624B located along the side walls 660A, 660B of the foam layer 650 can flex outward in a gentle bend in response to a sitting force applied to the top surface of foam layer 650. If the bus bars 624A, 624B are not bonded to the side walls 660A, 660B, the gentle bend outward may be approximately perpendicular to a downward sitting force. In some examples, not bonding the bus bars 624A, 624B to the side walls 660A, 660B, and thus having the bus bars 624A, 624B freely contained within the heated mattress 602, can protect against damage caused by downward forces causing sharp bending.

In some examples, the heater assembly 612 can include fabric side edge extensions 626A, 626B sewn to, adhesively attached to, or otherwise attached to the side edges 622A, 622B of the heating element 610, that can wrap around the side walls 660A, 660B of the foam compressible material layer 650 and attach (e.g., adhesively attach) to the bottom surface 654 (under side) of the foam layer 650. Woven, durable fabrics such as polyester can be used for the fabric side edge extensions 626A, 626B, however, other fabrics and films can be used. The adhesive attachments 642A, 642B of the fabric side edge extensions 626A, 626B to the foam layer 650 may be with pressure sensitive adhesives (PSA), hot-melt adhesives, air cured adhesives or UV cured adhesives, as non-limiting examples. Other adhesives and attachment techniques can be used.

In some examples, vertical slits 638A, 638B can be cut into the fabric side edge extensions 626A, 626B, allowing the heated mattress 602 to bend when the surgical table is bent into a "beach chair" configuration, requiring the heated mattress 602 to bend. The location of the vertical slits 638A, 638B can be determined by the location of the bend joint in the surgical table that the heated mattress 602 is configured to be used with.

In some examples, the heater assembly 612 is not adhesively attached to the whole top surface 652 of the foam layer 650, so as to allow movement of the heater assembly 612 against the foam layer 650 in order to reduce "hammocking." "Hammocking" is a term of art referring to added unwanted support and pressure against the skin that comes from a layer of fabric above a foam mattress acting like a "cot" (not a hammock)—the fabric is stretched from the sides, preventing the patient from sinking into the foam. We have found that if the heating element 610 is adhesively attached across all (or, in some instances, most) of the top surface 652 of the foam layer 650, a person laying on the heated mattress 602 can be prevented from optimally sinking into the foam layer 650. This can occur because the downward force (weight) of a person laying on the heated mattress 602 forces the heating element 610 into the foam layer 650. The relatively non-stretchable fabric of the heating element 610 can force the entire heating element 610 to pull from the sides 622A, 622B toward the center. If the heating element 610 is adhesively attached to the top surface 652 of foam layer 650, the entire top surface 652 of foam layer 650 can then be pulled toward the center and compressed. The need to displace that much foam laterally prevents the heating element 610 from optimally sinking into the foam layer 650 because of a so-called "hammocking" effect.

We have tested the effect of adhesively attaching heating element 610 to the top surface 652 of foam layer 650. In some such tests, a 2×4 piece of wood 11" long was cut with a serpentine cut parallel to the 4" sides to create three 1" high bumps. A pressure mapping mat was placed on top of a heated mattress 602 with the heating element 610 adhesively attached to the top surface 652 of foam layer 650. The wood piece was placed on top of the pressure mat with the bumps facing downward and 30 lbs. of weight were applied to the top surface of the piece of wood. The average pressure was 42.8 torr and the effective area in contact with the mattress 602 was 24.25 in². The same test was repeated with the heating element 610 not adhesively attached to the top surface 652 of foam layer 650. The average pressure was 30.5 torr and the effective area in contact with the mattress 602 was 32.5 in². Thus, these test results indicate that adhesively attaching the heating element 610 to the top surface 652 of foam layer 650 increases the contact pressure 42.8 torr vs. 30.5 torr and decreases the effective contact area 24.25 in² vs. 32.5 in². These test results indicate that the pressure against the patient's skin would be minimized by not adhesively attaching the heating element 610 to the top surface 652 of foam layer 650.

In some examples, especially in the case where the heated mattress 602 is going to be tipped into a steep Trendelenburg (head down) oriented position, it can be advantageous to adhesively secure some or all of the heating element 610 to one or more of the foam layer 650, the shell 666 or any other layer that have been interposed, in order to help prevent the layers from slipping on each other when gravity tries to pull the patient down the incline. Maintaining the pressure off-loading enhancement of avoiding adhesively attaching the heating element 610 to the top surface 652 of foam layer 650 as disclosed above can be achieved at least in part by partially adhering the layers. For example, as shown in FIG. 21, a longitudinal strip of adhesive 642C (e.g., 4-6 inches in width) can be applied along the midline which will stabilize the heating element 610 with respect to either the foam layer 650 or the shell 666. Other widths and shapes of adhesive can be. This may be protective from the longitudinal forces exerted by the weight of a patient in the Trendelenburg position causing sliding between the foam layer 650 and the heating element 610, while simultaneously helping to allow the heating element 610 to pull from the side edges 622A, 622B toward the midline, helping to minimize hammocking as previously discussed. In some examples, limiting the adhesive bond to a strip down the midline can allow the heater fabric of heating element 610 to freely pull in from the edges, relative to the foam layer 650 that it is bonded to along the midline. In some examples, the heating element 610 may be adhesively bonded to the foam layer 650 or the shell 666 using pressure sensitive adhesives (PSA), hot-melt adhesives, air cured adhesives, or UV cured adhesives. Other adhesives and attachment techniques can be used.

In some examples, partial adhesive attachment of the heating element 610 to the foam layer 650 may be a strip of adhesive (e.g., 6-12 inches in width) applied transversely, substantially from side wall 660A to side wall 660B in the area corresponding to the bend in the surgical table at which the heated mattress 602 is to be used. When the heated mattress 602 is bent and the heating element 610 is not attached to the foam layer 650, the heating element 610 can "ruck" or bunch up at the bend, doubling or even tripling the heat output at the bend and may cause a burn to a patient. If the heating element 610 is adhesively attached to the foam layer 650, bending the mattress 602 will naturally cause transverse indentations into the foam layer 650 that pull the attached heating element 610 material into the indentation away from patient contact, helping to safely prevent rucking and overheating.

In some examples, the heater assembly 612 may be covered on a top surface 614 and/or a bottom surface 616 with a layer of oxygen barrier polymeric film 644, 646, helping to protect the heating element from oxidizers such as peroxide and oxygen. In some examples, the oxygen barrier polymeric film 644, 646 may be adhesively bonded to the heating element 610. One example of an oxygen barrier polymeric film is GX-P-F from Toppan, which has a PET/AIOX, 48 ga base layer and EVOH barrier coat layer. Another common oxygen barrier polymeric film is PVDC film. Other films can be used. In some examples, the oxygen barrier polymeric film 644, 646 may be adhesively bonded to the heating element 610 using pressure sensitive adhesives (PSA), hot-melt adhesives, air cured adhesives or UV cured adhesives. Other adhesives and attachment techniques can be used.

In some examples, as shown in FIG. 21, a thin layer of foam 676 may be positioned between the heating element 610 and the shell 666. In some examples, this thin layer of foam 676 may be between ⅛ inch and ⅜ inch thick. In some examples, this thin layer of foam 676 may be made of durable urethane foam although other foams can be used. In some examples, this thin layer of foam 676 may be adhesively bonded to the heating element 610 across some or all of the top surface 614 of the heating element 610. In some examples, this thin layer of foam 676 may not be bonded to the shell 666 but the porous foam interacts with the knit fabric backing material of the shell 666 creating friction that prevents slippage between these two layers. Avoiding adhesive between the thin layer of foam 676 and the shell 666 can help to maximize conformability and compressibility, while maintaining stability of the shell 666 in the presence the deforming force vector created by gravity trying to pull the patient down and off the surgical table in the Trendelenburg position. The thin layer of foam 676 can also make the upper surface of the heated mattress 602 feel much softer to the touch compared to positioning the heating element 610 directly under the shell 666.

In some examples, a pressure sensor 636 can be included at the heated mattress 602, such as near the temperature control sensor 634, to detect the presence or absence of a patient laying on the mattress 602, including, for instance, detecting the presence of a patient laying on the temperature control sensor 634. When the temperature control sensor 634 is exposed to air (no patient), a heating element 610 that produces a uniform heat output across its surface can get very warm in an area covered by a thermal insulator such as a pile of blankets placed on the mattress 602, but not covering the temperature control sensor 634. This scenario could happen for example if the heated mattress 602 was left on at the end of surgery and a pile of blankets or a pillow was conveniently left setting on the mattress 602. In some examples, the temperature of the heating element 610 might be automatically turned down or even turned off if the pressure sensor 636 does not detect the weight of a patient on the mattress 602 for a preset period of time—for example 5 minutes, 10 minutes, 15 minutes, etc. This can help to prevent the heated mattress 602 from over-heating in an area under a thermal insulator such as a pile of blankets for example. The preset time limit can allow preheating of the mattress 602 before surgery but does not allow enough time to significantly overheat under a pile of blankets. In some examples, the heating element 610 may not turn on unless the pressure sensor 636 detects the weight of a patient on the mattress 602.

In some examples, especially in the case where the heated mattress 602 is going to be tipped into a steep Trendelenburg (head down) position, it may be advantageous to reinforce the foam layer 650 at the lower wall 658 (foot end), strengthening it against the significant force created by a relatively larger patient (e.g., a 400 pound patient) trying to slip down the steep incline. Certain securement devices such as WaffleGrip® may be anchored to or wrapped over end of the mattress 602 at the perineal cutout 662, further increasing the pressure applied to that part of the mattress 602.

In some examples, a fabric lower edge extension 630 is attached to the lower edge 620 of the flexible sheet-like heating element 610 and is attached (e.g., adhesively attached) to one or more of the top surface 652, the lower wall 658 and the bottom surface 654 of the foam layer 650. The fabric lower edge extension 630 may be attached to the foam layer 650 walls within the perineal cutout 662 and adjacent the perineal cutout 662 to reinforce the perineal cutout 662 against pressures applied to it during Trendelenburg securement. In some examples, a substantially "U" shaped perineal cutout reinforcement 632 may be added as an additional layer to the top surface 652 of the foam layer 650 at the perineal cutout 662. Perineal cutout reinforcement 632 may be sewn or adhesively bonded to the fabric lower edge extension 630 and/or adhesively bonded to the top surface 652 of the foam layer 650 at the perineal cutout 662. Perineal cutout reinforcement 632 may include wings that engage with and are bonded to the foam layer 650 at the vertical side walls of at the perineal cutout 662 creating an advantageous force vector directly opposite the force vector created by gravity trying to pull the patient down and off the surgical table in the Trendelenburg position. Perineal cutout reinforcement 632 reinforces the lip of the perineal cutout 662 against crushing by a WaffleGrip® securement device that may be wrapped over the perineal cutout 662 and secured under the heated mattress 602 or under the perineal cutout in the surgical table as shown in FIG. 23.

In some examples, the WaffleGrip® securement device is a sheet of fabric that includes friction enhancing elements applied to at least a portion of the upper surface, that can be placed on top of the heated mattress 602, preventing a patient from sliding off surgical table when placed in the steep Trendelenburg (head down) position. WaffleGrip was invented and developed by the inventors of the instant disclosure and currently includes five issued US patents: U.S. Pat. Nos. 10,765,580; 10,980,694; 10,993,866; 10,575,784; and 10,959,675. In some examples, it may be advantageous to anchor the foot end of any securement device, including but not limited to WaffleGrip, directly to the foot end of the surgical table, in the perineal cutout 662.

Figure 22:
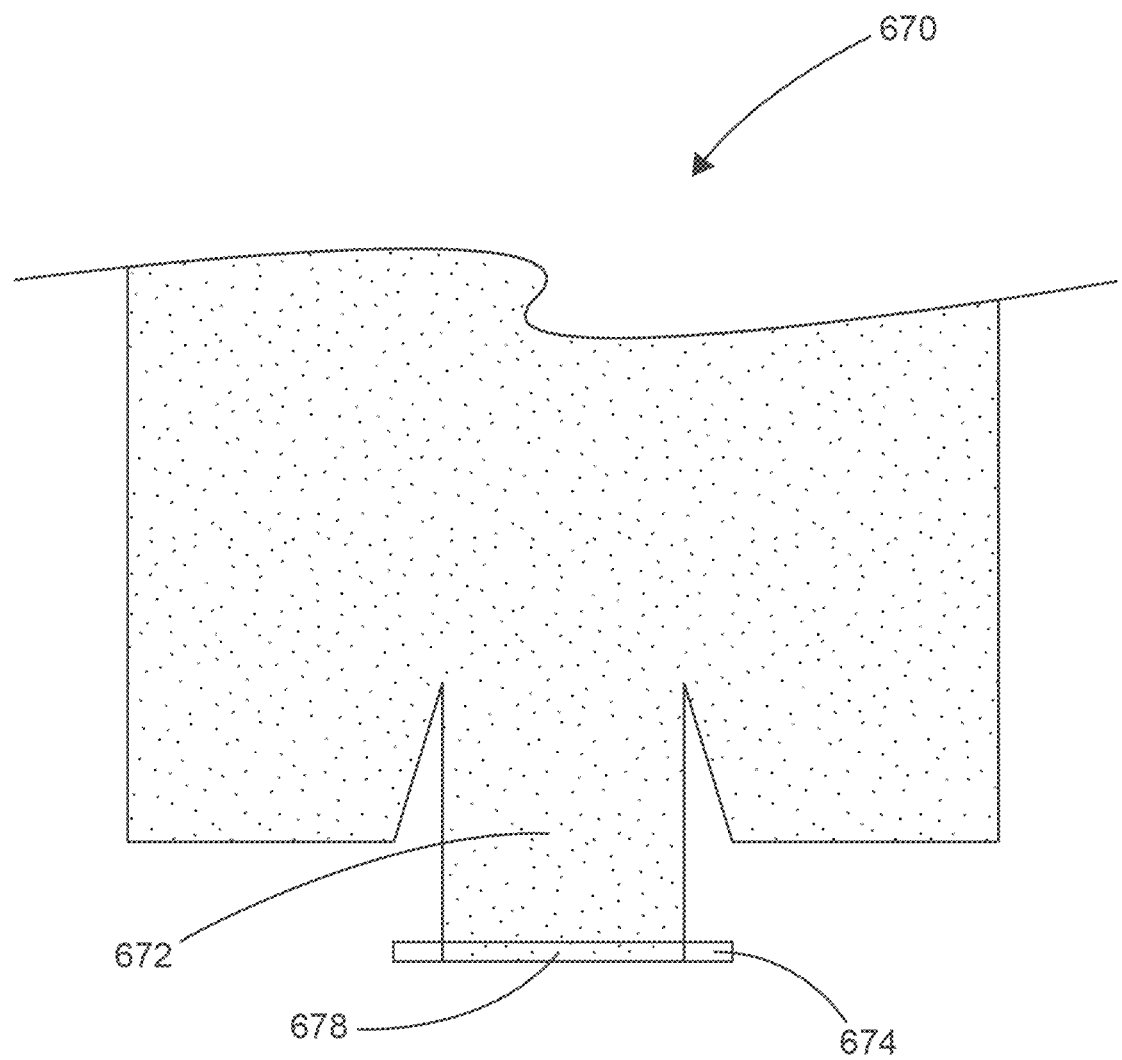
FIG. 22 is a partial top plan view of a securement device that can be used with the heated mattress, such as that shown in FIG. 18, in accordance with embodiments of the invention.
Figure 23:
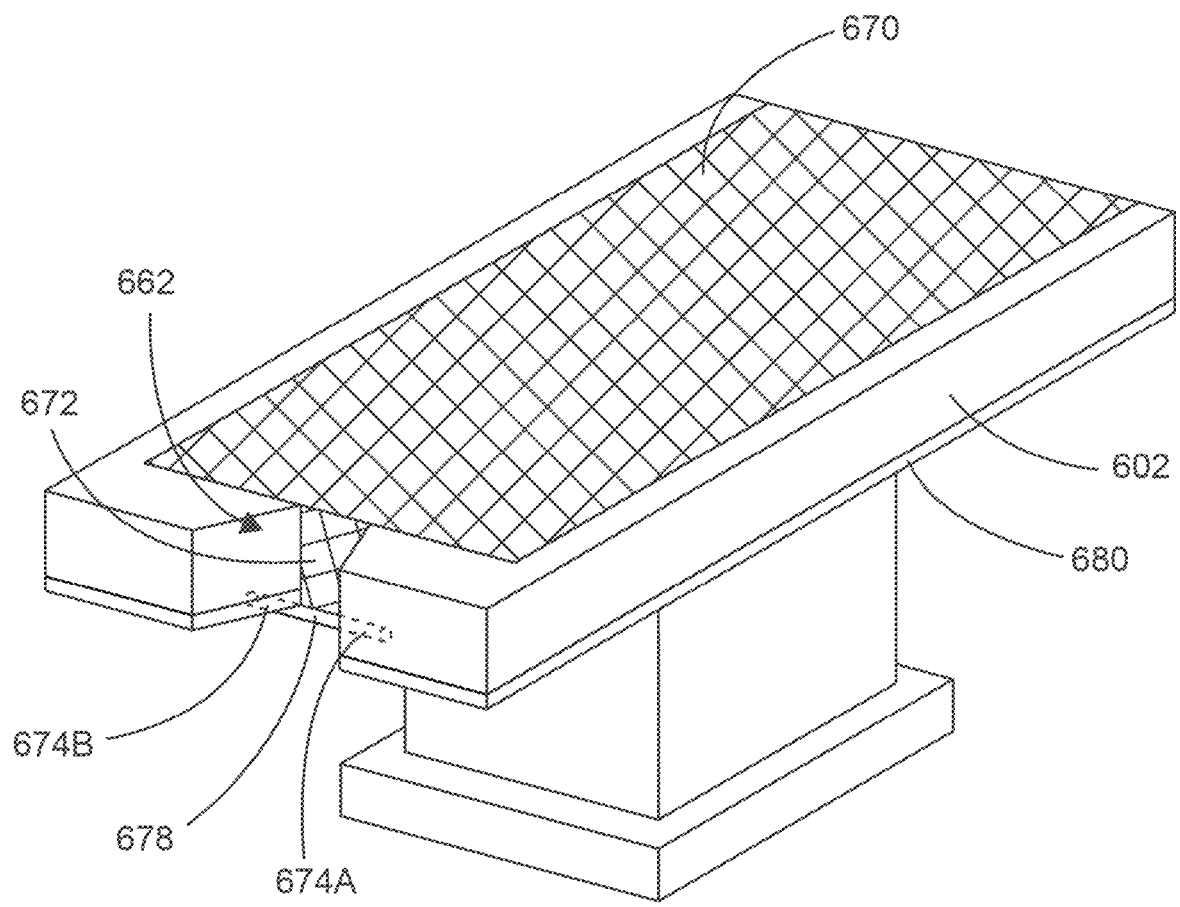
FIG. 23 is a perspective view of the securement device of FIG. 22 attached to a heated mattress, such as that shown in FIG. 18, on an operating table in accordance with embodiments of the invention.

In some examples as shown in FIGS. 22 and 23, the foot end of a securement device 670 may have an extension 672 that can be approximately the width of the inner wall of perineal cutout 662. In some examples, the surgical table has a perineal cutout that matches the size and shape of the perineal cutout 662 of the heated mattress 602. In some examples, the length of the extension 672 at the foot end is approximately equal to the combined thickness or height of the heated mattress 602 and the thickness or height of the surgical tabletop. In some examples, a rod 674 is attached to the distal end of the extension 672 at the foot end. The portions of the rod 674A, 674B protruding laterally from the extension 672 at the foot end can be hooked under the tapered sides of the perineal cutout 662 in the surgical tabletop. In this location, the extension 672 at the foot end is positioned vertically against the foot end of the surgical mattress in the perineal cutout 662. This can allow the securement device 670 to be easily and quickly anchored directly to the surgical tabletop, for increased security. Anchoring directly to the surgical table can be much more secure than anchoring to the surgical mattress which is both flexible, deformable and secondarily anchored to the surgical table.

In some examples, anchoring the foot end of securement device 670 under the perineal cutout 662 of the surgical table creates a force vector directly opposite the force vector created by gravity trying to pull the patient down and off the surgical table in the Trendelenburg position. This is in contrast to prior securement devices that anchor to the side rails of the surgical table. Anchoring to the side rails creates a much less efficient, lateral or tangential force vector to counter the force vector created by gravity trying to pull the patient down and off the surgical table in the Trendelenburg position. Anchoring to the side rails can frequently allow an anchoring device to slide against the table mattress for a distance down the incline created by the Trendelenburg position, before anchoring straps eventually rotate from lateral to tangential and tightening. Any sliding during Trendelenburg positioning in robotic surgery can be hazardous for the patient.

Rod 674 may be made of any rod-shaped material including but not limited to plastic, wood or metal and may or may not be round in cross section. In some examples, rod 674 may be made of inexpensive PVC pipe between ⅜ inch and ¾ inch in diameter. In some examples, the cut ends of rod 674 may be covered with plastic caps. In some examples, rod 674 may be secured to the extension 672 at the foot end of securement device 670 by wrapping the extension at the foot end 672 back on to itself creating a pouch 678 that can accommodate, and receive, the rod 674. The extension 672 at the foot end and the wrapped distal end of the extension 672 at the foot end may be bonded together with an RF seal, ultrasonic seal, heat seal, sewing or adhesive bond to create the pouch 678 for receiving the rod 674.

In some examples, the lower wall 658 and perineal cutout 662 may be further reinforced by inserting a relatively stiff reinforcing plate 668 of thin material under the foam layer 650. The reinforcing plate 668 may be between 6 inches and 24 inches long and extend substantially from one side wall 660A to the other side wall 660B of the foam layer 650. Following the shape of the lower wall 658, the reinforcing plate 668 may include a perineal cutout 662. In some examples, the reinforcing plate 668 may be made of plastic such as polyethylene or PVC in sheets that may be 0.050 inch to 0.3 inch thick. In some examples, the reinforcing plate 668 may be made of metal or wood. Other materials and thicknesses can be used. In some examples, the reinforcing plate 668 may be inserted between the layers of foam when the foam layer 650 is constructed with laminated layers of different foams.

Heated mattress 602 may be covered on one or more (e.g., all) sides in a flexible shell material that typically is made of a PVC film extruded onto a woven or knit fabric layer. The shell 666 may be sewn or ultrasonically bonded to produce a water-proof protective housing for the heated mattress 602.

In the foregoing detailed description, the invention has been described with reference to specific embodiments. However, it may be appreciated that various modifications, changes and alternative combinations can be made without departing from the scope of the invention as set forth in the appended claims. Although embodiments of the invention are described in the context of a hospital operating room, it is contemplated that some embodiments of the invention may be used in other environments. Those embodiments of the present invention, which are not intended for use in an operating environment and need not meet stringent FDA requirements for repeated used in an operating environment, need not including particular features described herein, for example, related to precise temperature control. Thus, some of the features of preferred embodiments described herein are not necessarily included in preferred embodiments of the invention which are intended for alternative uses.

What is claimed is:

1. An electric heating pad for warming a patient, the electric heating pad comprising a heated underbody support or heated mattress, the heated underbody support or heated mattress comprising:
    a heater assembly comprising:
        a flexible sheet-like heating element including a top surface, a bottom surface, an upper edge, a lower edge, and at least two side edges,
        conductive bus bars including a first conductive bus bar attached near one of the at least two side edges of the heating element and a second conductive bus bar attached near another of the at least two side edges of the flexible sheet-like heating element, and
        fabric side edge extensions extend from the at least two side edges of the flexible sheet-like heating element;
    a layer of polymeric foam including a top surface, a bottom surface, an upper wall, a lower wall, and at least two side walls, the layer of polymeric foam positioned under the heater assembly; and
    a shell covering at least a portion of the heater assembly and the layer of polymeric foam, the shell comprising one or more sheets of flexible material,
    wherein the heater assembly is wrapped around the top surface of the layer of polymeric foam and the at least two side edges of the flexible sheet-like heating element extend partially down the at least two side walls of the layer of polymeric foam and the conductive bus bars lie adjacent the at least two side walls of the layer of polymeric foam, and
    wherein the fabric side edge extensions are wrapped under and attached to the bottom surface of the layer of polymeric foam thereby securing the heater assembly to the layer of polymeric foam.

2. The heating pad of claim 1, wherein the heater assembly is adhesively connected to the top surface of the layer of polymeric foam over less than an entirety of the top surface of the layer of polymeric foam.

3. The heating pad of claim 2, wherein the heater assembly is adhesively connected to the top surface of the layer of polymeric foam by a longitudinal midline adhesive strip 4-6 inches wide.

4. The heating pad of claim 1, wherein the heater assembly is adhesively connected to the top surface of the layer of polymeric foam at a location of the top surface of the layer of polymeric foam corresponding to an area of the heating pad that is configured to bend as a result of bending a surgical table into a sitting position.

5. The heating pad of claim 1, wherein the heater assembly is not adhesively connected to the at least two side walls of the layer of polymeric foam.

6. The heating pad of claim 1, wherein a layer of foam material is bonded to the top surface of the heater assembly to form an unbonded friction connection between the layer of foam and the shell.

7. The heating pad of claim 1, wherein the fabric side edge extensions of the heater assembly include vertical slits extending to and including the fabric side edge extensions that are attached to the bottom surface of the layer of polymeric foam, and wherein the vertical slits are at a location corresponding to an area of the heating pad that is configured to bend as a result of bending a surgical table into a sitting position.

8. The heating pad of claim 1, wherein the heater assembly includes at least one layer of polymeric oxygen barrier film attached to and covering at least one of the top surface and the bottom surface of the flexible sheet-like heating element.

9. The heating pad of claim 1, wherein the heater assembly further includes a temperature control sensor attached to the flexible sheet-like heating element at a location configured to be in contact with a patient laying on the heating pad, wherein the heater assembly further includes a pressure sensor located adjacent the temperature control sensor to detect a weight of a patient laying on the heating pad, and wherein the pressure sensor is configured to reduce or turn off electrical power to the flexible sheet-like heating element when the weight of the patient has not been detected by the pressure sensor for a preset period of time.

10. An electric heating pad for warming a patient, the electric heating pad comprising a heated underbody support or heated mattress, the heated underbody support or heated mattress comprising:
    a heater assembly comprising:
        a flexible sheet-like heating element including a top surface, a bottom surface, an upper edge, a lower edge, and at least two side edges,
        conductive bus bars respectively attached near each of the at least two side edges of the flexible sheet-like heating element,
        a temperature control sensor attached to the flexible sheet-like heating element at a location configured to be in contact with a patient laying on the electric heating pad,
        a pressure sensor to detect a weight of a patient laying on the electric heating pad, and
        fabric side edge extensions extend from the at least two side edges of the flexible sheet-like heating element;

a layer of polymeric foam including a top surface, a bottom surface, an upper wall, a lower wall, and at least two side walls, the layer of polymeric foam positioned under the heater assembly; and a shell covering the heater assembly and the layer of polymeric foam, the shell comprising one or more sheets of flexible material, wherein the heater assembly is wrapped around the top surface of the layer of polymeric foam and the at least two side edges of the flexible sheet-like heating element and the conductive bus bars lie adjacent the at least two side walls of the layer of polymeric foam, wherein the fabric side edge extensions are wrapped under and attached to the bottom surface of the layer of polymeric foam thereby securing the heater assembly to the layer of polymeric foam, and wherein the pressure sensor is configured to reduce or turn off electrical power to the flexible sheet-like heating element when the weight of the patient has not been detected by the pressure sensor for a preset period of time.

11. The heating pad of claim 10, wherein the heater assembly is adhesively connected to the top surface of the layer of polymeric foam over less than an entirety of the top surface of the layer of polymeric foam.

12. The heating pad of claim 11, wherein the heater assembly is adhesively connected to the top surface of the layer of polymeric foam by a longitudinal midline adhesive strip 4-6 inches wide.

13. The heating pad of claim 10, wherein the heater assembly is not adhesively connected to the at least two side walls of the layer of polymeric foam.

14. The heating pad of claim 10, wherein a width of the flexible sheet-like heating element is wider than a width of the top surface of the layer of polymeric foam, and wherein, the heater assembly is wrapped around the top surface of the layer of polymeric foam, the at least two side edges of the flexible sheet-like heating element extend partially down the at least two side walls of the layer of polymeric foam and the conductive bus bars lie adjacent the at least two side walls of the layer of polymeric foam.

15. An electric heating pad for warming a patient, the electric heating pad comprising a heated underbody support or heated mattress, the heated underbody support or heated mattress comprising:

a heater assembly comprising:
  a flexible sheet-like heating element including a top surface, a bottom surface, an upper edge, a lower edge, and at least two side edges,
  conductive bus bars respectively attached near each of the at least two side edges of the flexible sheet-like heating element,
  fabric side edge extensions extend from the at least two side edges of the flexible sheet-like heating element, and
  a fabric lower edge extension attached to the lower edge of the flexible sheet-like heating element;

a layer of polymeric foam including a top surface, a bottom surface, an upper wall, a lower wall, at least two side walls, the layer of polymeric foam positioned under the heater assembly; and a shell covering the heater assembly and the layer of polymeric foam, the shell comprising one or more sheets of flexible material, wherein the heater assembly is wrapped around the top surface of the layer of polymeric foam and the at least two side edges of the flexible sheet-like heating element and the conductive bus bars lie adjacent the at least two side walls of the layer of polymeric foam, wherein the fabric side edge extensions are wrapped under and attached to the bottom surface of the layer of polymeric foam thereby securing the heater assembly to the layer of polymeric foam, and wherein the fabric lower edge extension, attached to the lower edge of the flexible sheet-like heating element, is attached to the top surface, the lower wall and the bottom surface of the layer of polymeric foam.

16. The heating pad of claim 15, wherein the heater assembly is adhesively connected to the top surface of the layer of polymeric foam over less than an entirety of the top surface of the layer of polymeric foam.

17. The heating pad of claim 16, wherein the heater assembly is adhesively connected to the top surface of the layer of polymeric foam by a longitudinal midline adhesive strip 4-6 inches wide.

18. The heating pad of claim 15, wherein the heater assembly is not adhesively connected to the at least two side walls of the layer of polymeric foam.

19. The heating pad of claim 15, wherein a layer of foam material is bonded to the top surface of the heater assembly to form an unbonded friction connection between the layer of foam and the shell.

20. The heating pad of claim 15, wherein the heater assembly further includes a temperature control sensor attached to the flexible sheet-like heating element at a location configured to be in contact with a patient laying on the heating pad, wherein the heater assembly further includes a pressure sensor located adjacent the temperature control sensor to detect a weight of a patient laying on the heating pad, and wherein the pressure sensor is configured to reduce or turn off electrical power to the flexible sheet-like heating element when the weight of the patient has not been detected by the pressure sensor for a preset period of time.

21. The heating pad of claim 15, wherein the fabric side edge extensions of the heater assembly include vertical slits extending to and including the fabric side edge extensions that are attached to the bottom surface of the layer of polymeric foam, and wherein the vertical slits are at a location corresponding to an area of the heating pad that is configured to bend as a result of bending a surgical table into a sitting position.

* * * * *